(12) United States Patent
Bianco

(10) Patent No.: US 7,922,850 B2
(45) Date of Patent: Apr. 12, 2011

(54) CLOSURE ELEMENT FOR ABSORBENT SANITARY PRODUCTS, MANUFACTURING PROCESS, PROCESS OF USE, AND PRODUCT THUS OBTAINED

(75) Inventor: Carlo Bianco, Pescara (IT)

(73) Assignee: Fameccanica.Data S.p.A, Sambuceto di San Giovanni Teatino (IT)

( * ) Notice: Subject to any disclaimer, the term of this patent is extended or adjusted under 35 U.S.C. 154(b) by 569 days.

(21) Appl. No.: 11/999,990

(22) Filed: Dec. 6, 2007

(65) Prior Publication Data

US 2008/0099124 A1 May 1, 2008

Related U.S. Application Data

(62) Division of application No. 10/965,016, filed on Oct. 13, 2004, now Pat. No. 7,326,191.

(30) Foreign Application Priority Data

Oct. 13, 2003 (EP) .................................. 03425661
Aug. 20, 2004 (EP) .................................. 04019792

(51) Int. Cl.
*A61F 13/15* (2006.01)
(52) U.S. Cl. ................... 156/204; 156/256; 156/227
(58) Field of Classification Search .............. 156/256, 156/204, 227; 604/385.03, 385.04, 385.05
See application file for complete search history.

(56) References Cited

U.S. PATENT DOCUMENTS

| | | | |
|---|---|---|---|
| 4,610,680 A | 9/1986 | LaFleur | 604/385 |
| 5,624,428 A | 4/1997 | Sauer | 604/391 |
| 5,855,574 A | 1/1999 | Kling et al. | 604/392 |
| 6,210,388 B1 | 4/2001 | Widlund et al. | 604/390 |
| 6,210,390 B1 | 4/2001 | Karlsson | 604/391 |
| 6,328,725 B2 * | 12/2001 | Fernfors | 604/391 |
| 6,409,858 B1 | 6/2002 | Popp et al. | 156/66 |
| 6,447,628 B1 | 9/2002 | Couillard et al. | 156/204 |
| 6,461,344 B1 | 10/2002 | Widlund et al. | 604/390 |
| 6,477,628 B1 | 11/2002 | Bish et al. | 711/162 |
| 7,132,031 B2 | 11/2006 | Ohiro et al. | 156/270 |
| 2002/0111596 A1 * | 8/2002 | Fletcher et al. | 604/385.03 |
| 2003/0018315 A1 | 1/2003 | Popp et al. | 604/386 |
| 2005/0038405 A1 | 2/2005 | Shimoe | 604/389 |

FOREIGN PATENT DOCUMENTS

| | | |
|---|---|---|
| EP | 0 943 305 | 9/1999 |
| EP | 0 943 395 A2 | 9/1999 |
| EP | 0 997 123 A1 | 5/2000 |

* cited by examiner

*Primary Examiner* — Khanh Nguyen
*Assistant Examiner* — Vishal I Patel
(74) *Attorney, Agent, or Firm* — Seed IP Law Group PLLC

(57) ABSTRACT

A process is provided for making a fastening element for absorbent sanitary products having first and second parts that are symmetrical with respect to an intermediate plane, each part including a base branch connectable to the first part, and a distal branch connectable to the second part. The base branch and the distal branch are connected together according to a general book-like configuration. A dorsal part of the book-like configuration for connection between the base and the distal branches is set at a distance from said intermediate plane, the base branch connects the two parts to form a single body, each of which can connect mutually facing edges of the end parts of an absorbent sanitary product and to ensure the fastening of the flaps set on the sides. The fastening element can enable releasing and refastening the product and/or adjusting the fit of the product to the wearer's body.

12 Claims, 11 Drawing Sheets

CLOSURE ELEMENT FOR ABSORBENT SANITARY PRODUCTS, MANUFACTURING PROCESS, PROCESS OF USE, AND PRODUCT THUS OBTAINED

CROSS-REFERENCE TO RELATED APPLICATION

This application is a divisional of U.S. patent application Ser. No. 10/965,016, filed Oct. 13, 2004, now pending, which application is incorporated herein by reference in its entirety.

BACKGROUND

1. Technical Field

The present invention relates to absorbent sanitary products and has been developed with particular attention paid to its possible application to absorbent sanitary products that can be worn like a pair of pants. A typical example of absorbent sanitary products of this type is represented by baby diapers or the like.

2. Description of the Related Art

For many years now, the solution adopted in a practically uniform way by all the manufacturers of the sector has been that of making these products in the form of elements shaped according to a general hourglass configuration, with a central body, in which there is provided a composite absorbent structure designed to absorb body fluids, and two end parts, a front one and a rear one, which extend laterally. The product is put on, bestowing on it a general U-shaped configuration and bringing the median stretch of the central body up to the area where the legs of the user are inserted. The end parts are extended around the waist of the user, connecting the mutually opposed side edges thereof together by means of adhesive labels or stickers, which can normally be re-positioned, or similar fastening elements in such a way as to be able to refasten the product around the body of the user.

These products have been traditionally manufactured and sold in the open condition, i.e., leaving to the person who applies the product the task of setting it around the body of the user and of fastening it according to a general pant-like conformation in the way referred to previously.

In the course of the last few years, there has emerged a renewed interest in diapers of the type commonly referred to as "training pants". These are diapers of the type illustrated, for example, in the document U.S. Pat. No. 4,610,680, which are designed for being packaged and sold in a closed condition. When the product is taken out of the packaging, it has a conformation basically resembling that of a pair of pants. It is put on by making it slide over the legs of the user according to criteria basically similar to those followed for putting on a pair of pants. In view of the specific use to which the product is to be put, it is then envisaged that the product can be removed without having to slide it again over the legs of the user.

For this purpose, the product can be made in such a way as to be tearable (according to the criteria illustrated, precisely, in U.S. Pat. No. 4,610,680), or else by making the product so that it can be opened along the sides of the waist line, i.e., in an area of what may be defined the side flaps (as in the case of diapers of a traditional type, which are packaged and sold in the open condition), for example by envisaging the use of adhesive labels or stickers, sets of buttons, sets of press-studs or, according to a solution that has enjoyed a particular success, by envisaging the use of microhook fastening structures (also referred to as "Velcro fasteners").

The use of such fastening elements must be reconciled with the need, to which reference has already been made previously, to have the training pant preferably produced and packaged in a closed condition, so as to enable it to be put on like a normal pair of pants.

Various patent documents deal with the problem of applying these fastening elements in the framework of an industrial cycle that can be implemented In a context compatible with the high production rates that are typical of the sector.

In this connection, reference may be made, for instance, to the documents U.S. Pat. No. 5,855,574, U.S. Pat. No. 6,210,388, U.S. Pat. No. 6,409,858, U.S. Pat. No. 6,447,628, and U.S. Pat. No. 6,461,344.

The above documents, which do not, however, exhaust the entire field on the subject, deal with the problem of the application of the aforesaid fastening elements by drawing particular attention to the functionality of the end product.

At least some of these documents of course take into account the need to make the corresponding products at typical industrial production rates. For this reason, they suggest, according to different modalities, resorting to production processes of a continuous type, in which the products are made starting from the individual component parts, operating preferentially on a continuous chain of products designed for being separated from one another, so as to arrive at the formation of the individual products only in the final stages of the process.

However, above all as regards the application of the aforesaid fastening elements, the solutions described in these prior documents do not take into account various problems that can assume a considerable importance both at the level of manufacture and at the level of use of the products in question.

In the first place, during fabrication of the sanitary product, in the process of apply a fastening element (or a part of said element) on a strip, web or chain, the aforesaid strip, web or chain moves along at a relatively high linear speed, and may expose the aforesaid element, when it is not completely anchored to the strip, web or chain on which it is applied, to flap or move. Movement of the strip during fabrication may cause the element itself to be positioned improperly for subsequent operations of treatment, in particular as regards possible operations of cutting.

Furthermore, it is necessary to take into account the fact that the cutting operation for separating the individual sanitary products or the type of connection of the side edges used, can lead to the formation of elements or surfaces of friction which, if not appropriately shielded, may give rise to even rather disagreeable drawbacks, for instance irritation or cutting of the skin, since they directly face the body of the user.

Furthermore, it is important to prevent the user (typically, for instance, a baby, perhaps even a very small baby) from possibly opening, with the application of even a modest force, the flaps set on the sides and causing undesirable release of the fastening element, in particular in the case of absorbent products designed to be refastenable.

BRIEF SUMMARY

The purpose of the present invention is to provide a fastening element that is able to solve at least one and, in the currently preferred embodiments, all of the problems outlined above.

According to the present invention, this purpose is achieved due to a fastening element having the characteristics recalled specifically in the claims that follow.

The invention also relates to a corresponding process of fabrication and a corresponding method of use in order to obtain an absorbent sanitary product. As will emerge more clearly from what follows, the said process and method are suited for being possibly integrated together and for being carried out one after another in the sequence of a single process. Finally, the invention also regards the absorbent sanitary product thus made.

In the currently preferred embodiments, the fastening element according to the invention is configured as a sort of closed packet, without folds or similar configurations, which can be opened at the moment of cutting, transfer and positioning of the element on the structure of absorbent articles, such as diapers.

The above is possible thanks to the particular shape adopted, which is preferably an omega shape (and which preferably envisages the use of a single type of material for the main constituent element), with the added possibility of applying provisional seal formations, which can be removed during use of the product, for better conservation during manufacture of the closed-packet structure referred to previously.

The solution described leads to the production of a fastening element, which, thanks to the structure and to the material used for the main constituent element, makes it possible to achieve a continuous and delicate contact or feel (the so-called "soft touch") on the hips of the user so preventing any risk of causing irritation or cutting of the skin.

In addition, the solution described herein enables production of an absorbent sanitary product with flaps set on the closed sides by means of releasable elements, for example of the microhook (hook-and-loop), e.g., Velcro, type, or re-openable seal formations, for instance glue of the "evergreen" type (i.e., a glue which preserves its qualities over time, even following upon repeated detachment-reattachment of the connected parts), this glue also being referred to as "pressure-sensitive" glue, in which there is altogether prevented the eventuality of the user possibly forcing, by getting hold of any free flaps, the connection between the parts of the fastening element (in particular in the versions in which said fastening element is refastenable), so causing undesirable opening of the product.

It is important to note that in products of this sort, in which the flaps set on the sides of the product are not closed by means of re-openable elements, in order possibly to release and refasten the product it is necessary to tear the flaps.

BRIEF DESCRIPTION OF THE SEVERAL VIEWS OF THE DRAWINGS

The invention will now be described, purely by way of non-limiting example, with reference to the annexed drawings, in which.

DETAILED DESCRIPTION

In the various representations of FIGS. 1 to 18 and FIGS. 23 to 25, the fastening/closure element described herein is not drawn to scale. This fact can be appreciated e.g., by direct reference to FIGS. 19 and 20 and corresponds to a deliberate choice made for the sake of clarity of presentation.

Figure 19:
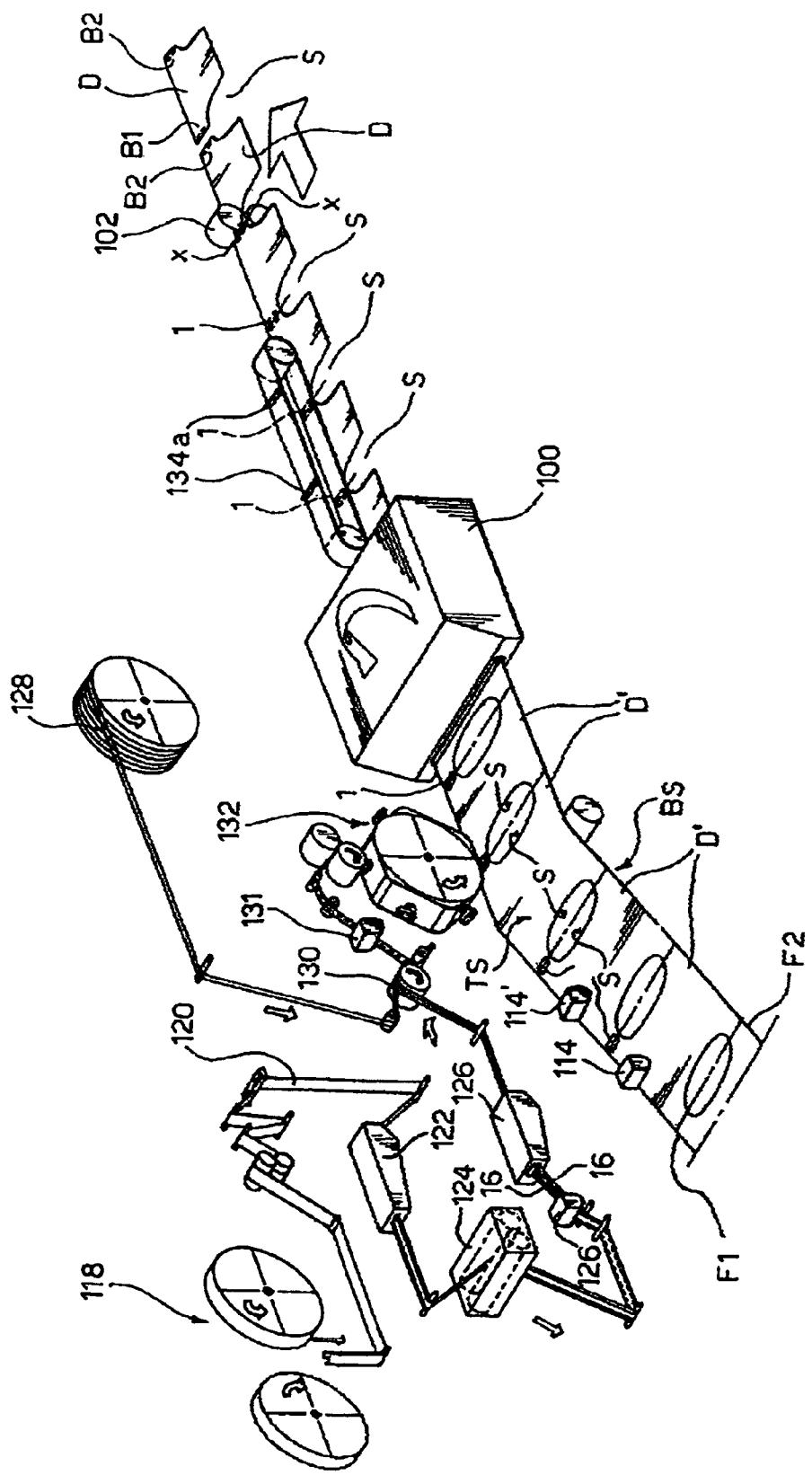
FIGS. 19 and 20 are schematic representations in perspective view of two possible solutions embodying equipment which, on the one hand, provides fastening elements according to some of the embodiments of the present invention and, on the other, applies the fastening elements thus produced on a chain of absorbent sanitary products that are being formed.
Figure 20:
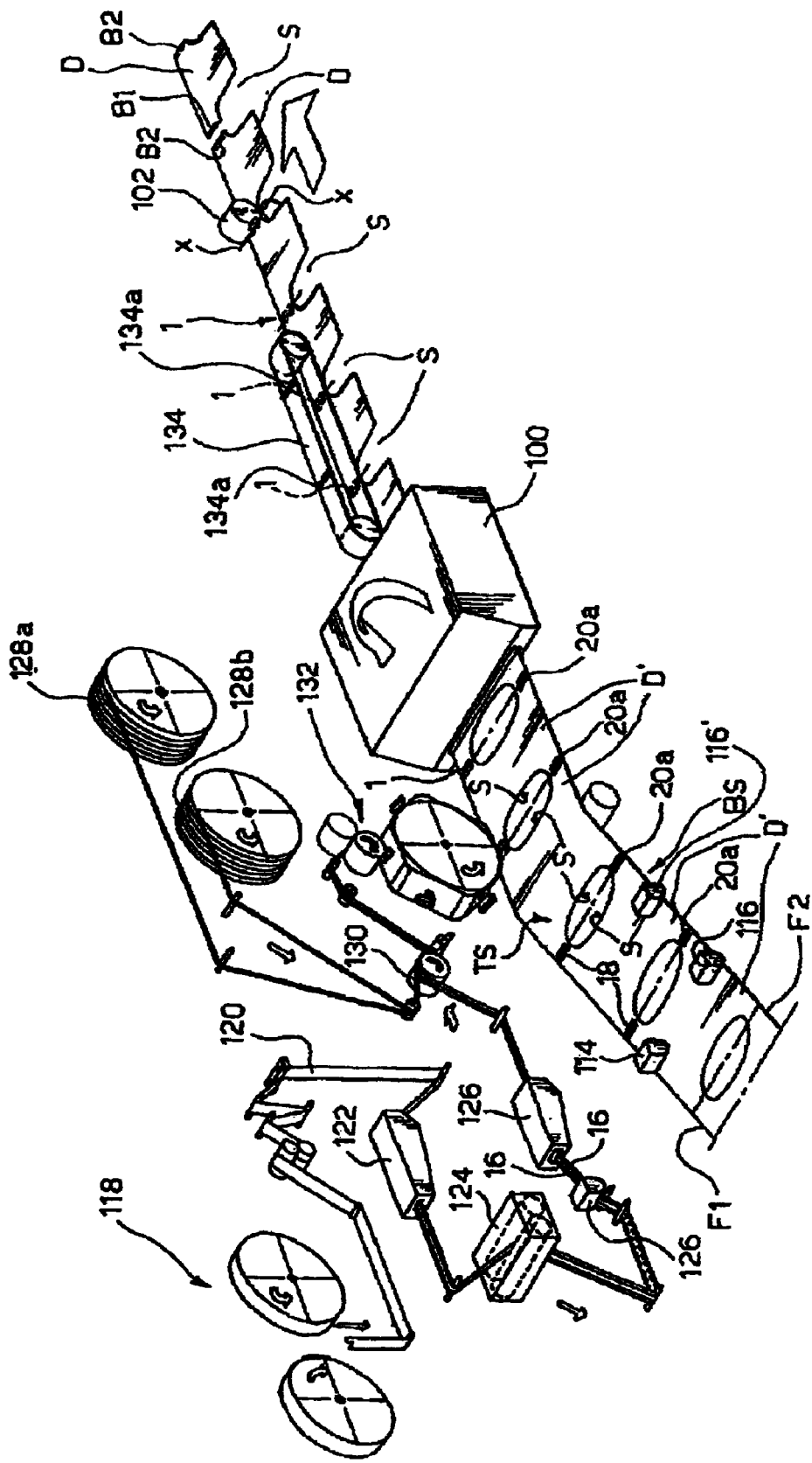

With immediate reference to FIGS. 19 and 20, in these figures the reference D indicates absorbent sanitary products such as diapers of the type commonly known as training pants.

FIGS. 19 and 20 refer to products made by operating crosswise.

This latter mode of operation, which is to be deemed known in its most general terms, envisages making a strip, web or chain of sanitary products (or, more correctly, of semi-finished pieces D' of said products), each of which presents a general hourglass configuration.

The semi-finished pieces D' are constituted by:
- a top or inner sheet (i.e., with respect to the normal conditions of use of the diaper), usually referred to as "topsheet" (TS), on which there can be set a pair of elasticized lateral barriers, which extend from one of the borders of said topsheet to the opposite border, and a pair of elastic or elasticized formations set centrally on the ends of said borders, in the direction orthogonal to said elasticized barriers;
- a backsheet (BS), i.e., a bottom or outer sheet or laminate (with respect to the normal conditions of use of the diaper), on which there may be set a pair of elastic or elasticized formations that extend from one of the borders of said backsheet to the opposite border; and
- an absorbent structure enclosed between said topsheet and said backsheet.

In the various FIGS. 2-3, 5-6, 8-9, 11-12, 14-15 and 17-18, the backsheet and the topsheet are designated, respectively, by the references BS e TS. The references TS and BS also appear in FIGS. 19 and 20.

The general hourglass configuration of the semi-finished pieces D' is the result of the generically widened pattern of the lateral end parts with respect to the sides of the central portion (or the area that remains adherent to the body) of each sanitary product, in which there are present parts S, which are cut out according to a general arched pattern (i.e., the cuts where the legs are inserted). Briefly, these are the parts which, in the diaper D closed to form a pair of pants, constitute the openings for the legs of the user (or passages for legs).

As is well known to persons skilled in the sector, the elastic or elasticized formations arranged centrally on the ends of the borders of the topsheet have the purpose of ensuring adherence of the waist line of the diaper to the abdomen of the user, whilst the elastic or elasticized formations which extend from one of the borders of said backsheet to the opposite border have the purpose of ensuring adherence of the passages for legs to the legs of the user.

The lateral end parts of the various semi-finished pieces D' are connected together so as to form the chain, strip or web already mentioned previously. For this reason, in the chain of semi-finished pieces D' represented at the bottom left in FIGS. 19 and 20, the cut-out parts S of the semi-finished pieces D' adjacent to one another are connected together to form, in the otherwise continuous body of the chain itself, approximately elliptical openings.

In a folding station 100, the chain of semi-finished pieces D' undergoes folding to form a V in the central region or adherent area of the hourglass configuration.

The operation of folding to form a V brings the opposed longitudinal margins F1 and F2 of the chain to overlap one another so as to form (according to criteria described more clearly in what follows) the waist lines of the individual products D. Simultaneously, the cut-out parts S come to form the passages for the legs in the products themselves.

The chain of products finally undergoes a cutting operation, implemented for example in a cutting station, designated by 102, which has a rotating-blade cutter. The cutting station 102 operates along the line identified by X-X in FIGS. 19 and 20 (the same indication appears—for reasons that will emerge more clearly from what follows—also in FIGS. 1-2, 4-5, 7-8, 10-11, 13-14 and 17-18). The cutting action brings about separation of the products D, which thus assume the character of individual products, which are to be sent on to a packaging station (not illustrated).

The general criteria for carrying out the operations just described are in themselves known in the prior art and do not require a detailed description herein, except as regards the elements that assume specific importance for the purposes of an understanding and implementation of the invention.

Persons skilled in the sector will understand that the characteristics and the modalities of application of the fastening elements 1, which will emerge more clearly from what follows, are to a large extent independent of the specific characteristics of embodiment of the various products D. This applies, in particular, but not exclusively, as regards the structure (or "construction") of the product D, i.e., as regards characteristics, such as the composition of the backsheet BS and of the topsheet TS and of the layers and auxiliary formations normally associated thereto, etc.

The fastening elements 1 described in what follows, in the embodiments represented in FIGS. 1 to 6, may be used in diapers of a training-pant type, which, once they have been brought into the closed position, cannot be re-opened unless they are torn.

Figure 7:
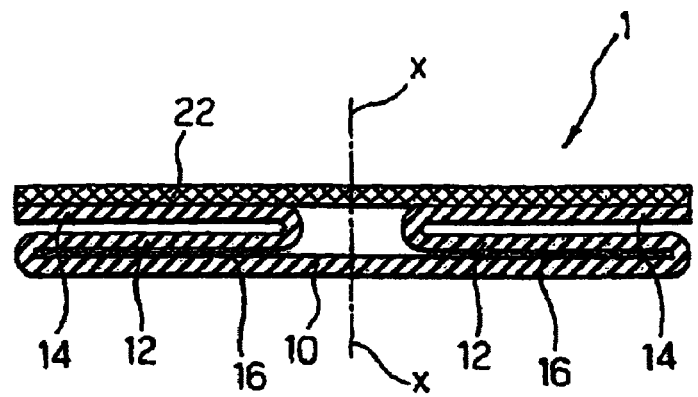
FIGS. 7 to 9 illustrate, once again according to criteria basically similar to the criteria of representation adopted in FIGS. 1 to 3, a third possible embodiment of a fastening element according to the invention.
Figure 8:
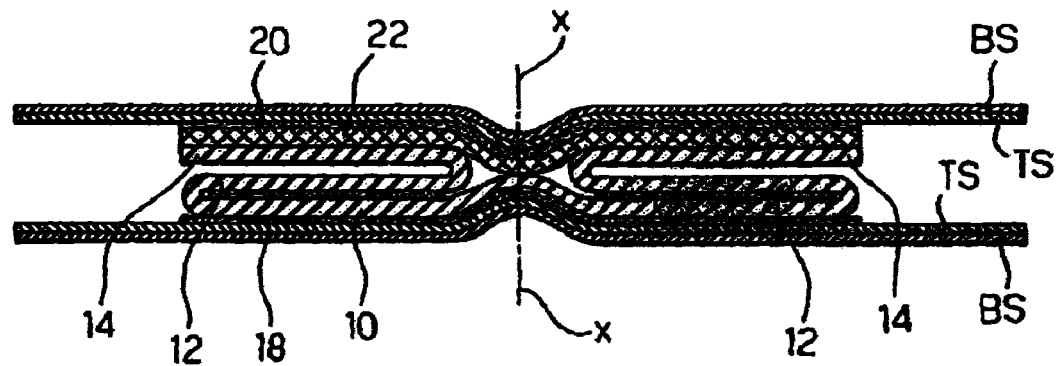
Figure 9:
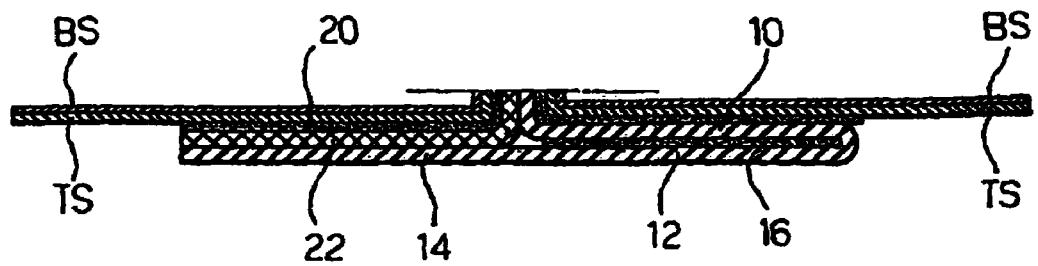

In the other embodiments represented—and in particular in the embodiments represented in FIGS. 7 to 9, which constitute the currently preferred embodiments of the invention— the fastening elements enable implementation of the function of release and refastening of the diaper, this being according to modalities that enable identification of the fastening element as releasable and refastenable.

It is to be noted how all the fastening elements 1 described enable diapers of a training-pant type to be made, which are characterized in that the flaps are set on the sides, in the normally closed condition, but are releasable and refastenable so as to enable access to the fastening elements in the case of diapers of the training-pant type (in which the fastening elements are of the releasable and refastenable type) and the subsequent fastening of the flaps themselves. In this way, since it is possible to prevent tearing of said flaps, and consequent exposure of the fastening elements of the releasable and refastenable type, any undesirable release of the diaper by the user is prevented.

The fastening elements 1, which are described more clearly in what follows, are designed for being located precisely in the areas of connection between the facing ends of two adjacent products D.

In FIGS. 19 and 20, the ends in question are designated, respectively, by B1 and B2 with reference to the (single) product D represented in the part furthest to the right in FIGS. 19 and 20, at output from the equipment illustrated herein. Furthermore, also designated by B2 is the end further downstream of the immediately adjacent product D.

Since the products D derive from the operation of folding to form a V performed in the station 100, each reference B1 and B2 actually identifies a pair of end borders (each corresponding to one of the margins F1 and F2 of the original chain constituted by the semi-finished pieces D' shaped like an hourglass).

As will emerge more clearly from what follows, the elements 1 have the function of connecting the end borders comprised in each of the aforesaid pairs, fastening the waist line of the respective products D following upon fastening of said end borders.

When the chain of products D illustrated in FIGS. 19 and 20 undergoes cutting along the line X-X in the station 102, the elements 1 are also cut along a median or basically median plane, thus being divided into two parts or halves.

Of these halves, a first half remains associated to the end B1 of a product D, by connecting the two corresponding borders, and a second half remains associated to the end B2 of the immediately adjacent product, also in this case by connecting the two corresponding borders.

If attention is paid precisely to the latter product D, which may be seen in the part furthest to the right in FIGS. 19 and 20, it may be understood how the fastening of the waist line of the product in question is ensured, at the end B1, by the first half of an element 1 and, at the end B2, by the second half of another element 1, which has been previously cut in the station 102.

Likewise, in the product D that immediately follows (namely, the one which, in FIGS. 19 and 20, appears as still undergoing the action of the cutting unit 102), the fastening of the waist line is ensured, at the end B2, by the second half of the element 1, the first half of which closes at the end B1 the product D further downstream and, at the end B1 (not, in actual fact, visible in the drawings in so far as it is hidden by the cutting unit 102), by the second half of another element 1, which is currently undergoing the action of the cutting unit 102.

The elements 1 can thus be used in a process for making sanitary products D, which can be worn like a pair of pants and which comprise opposed ends, which can be selectively connected to respective borders so as to define the waist line and the passage for legs of the sanitary product.

The process envisages, for this purpose, the operation of forming a chain of semi-finished pieces D' of absorbent sanitary products, in which semi-finished pieces that are adjacent in the chain are connected to one another at the aforesaid ends so as to form connection regions between successive semi-finished pieces in the chain. The said connection regions each have a center line (X-X), which extends in a direction transverse to the principal direction of extension and of advance of the chain of semi-finished pieces of sanitary products D'.

The fastening elements 1 are then applied (as will emerge more clearly from what follows) in the aforesaid connection regions, so causing the median plane of each fastening element 1—i.e., the plane which is also designated by X-X for immediate reference—to be aligned with the center line of a corresponding connection region.

The aforesaid semi-finished pieces of sanitary products are then re-closed on themselves according to a general V-shaped (or U-shaped) configuration, bringing the end parts of the semi-finished pieces into a position where they are facing one another with the interposition of the fastening elements 1.

The chain of semi-finished pieces of sanitary products is finally segmented along the center lines of the connection regions, so causing cutting of the fastening elements in their median plane X-X, with the corresponding division of the fastening elements into the aforesaid two parts or halves, which are basically symmetrical with respect to one another. These remain in their position, thus ensuring fastening of the waistline by means of closing of the side edges of the two individual products separated by the cutting action.

Figure 1:
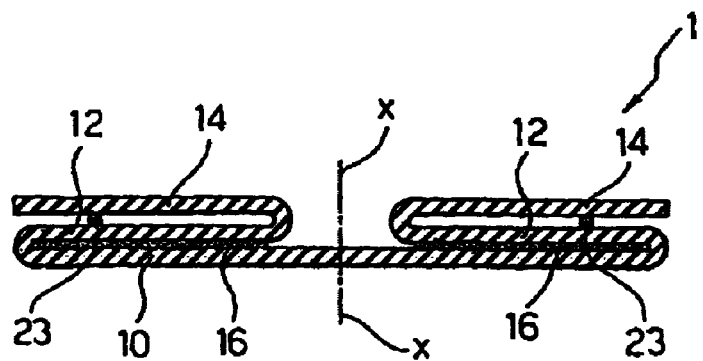
FIG. 1 is a cross-sectional view of a fastening element according to a first embodiment of the invention.
Figure 2:
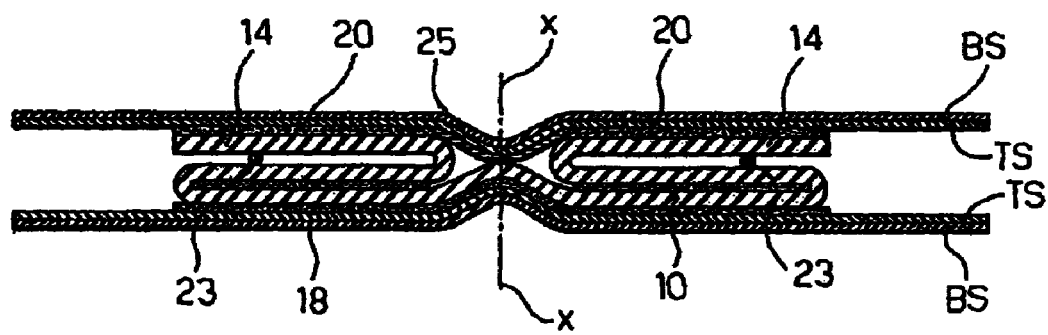
FIG. 2 illustrates the fastening element of FIG. 1 applied on two sanitary products comprised in a chain of products in the course of manufacture.
Figure 3:
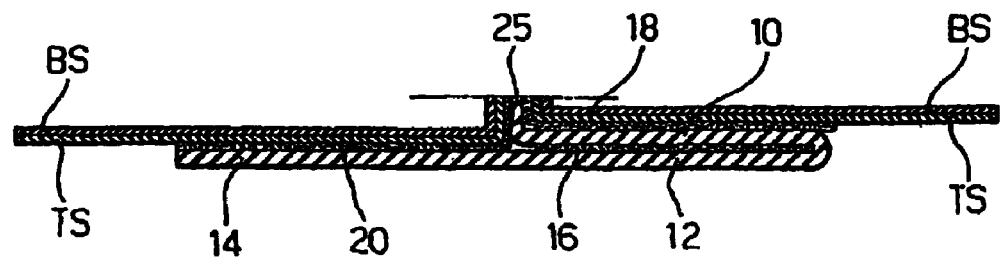
FIG. 3 illustrates the fastening element of FIG. 1 in its typical configuration of use, with the flap located on the sides closed.

The first embodiment of the fastening element 1 represented in FIGS. 1 to 3 practically corresponds to a base configuration.

The fastening element 1 represented in FIG. 1 is basically constituted by a strip of laminar material, such as a non-woven fabric, for instance of the type commonly referred to as SMS, folded according to a general omega-shaped configuration.

In practice, the element 1 in question comprises:
a base branch 10, which extends in a basically symmetrical way around the ideal line X-X along which the element 1 is then to be cut in the operation of separation carried out in the cutting station or cutting unit 102 described previously;
two intermediate branches 12, each of which is folded on the base layer so as to return towards the line X-X (without reaching it, to prevent undesirable effects of cutting, when the fastening element 1 is divided into two halves along the plane X-X); and
two distal stretches 14 turned up again on the intermediate stretches 12 so as to extend with their end borders approximately at the outer borders of the base branch 10 and of the loops or elbows that connect the intermediate stretches 12 with the borders of the base branch 10.

Of course, the choice of making the distal stretches 14 extend with their end borders approximately to the outer borders of the base stretch 10 is not to be considered in any way imperative. The distal stretches 14 can in fact be made so that they are both of equal length, either shorter or longer as compared to the corresponding portions of the base branch 10. The same also applies to the intermediate stretches 12.

The reference 16 designates a layer of glue designed to render the intermediate branches 12 fixed to the homologous parts of the base layer or base branch 10. It may, for instance, be a layer of glue of the hot-melt type or any other type commonly used for the connection of laminar products, such as, precisely, non-woven fabrics in the sanitary-products industry.

The reference number 23 designates provisional-seal formations that can render the intermediate stretches 12 fixed to the corresponding distal stretches 14. These provisional-seal formations can be made with the application of spots of evergreen or pressure-sensitive glue or by means of welding spots of a thermo-mechanical type (heat sealing).

Essentially, the fastening element just described comprises two parts or halves, which are basically symmetrical with respect to a median plane X-X. Each of these two parts in turn comprises a base-branch portion 10 and a distal branch 14 connected together according to a general book-like configuration, which is open towards the outside of the element 1 by means of the intermediate stretch 12.

The base branch 10 connects together the aforesaid two basically symmetrical parts so as to form a single element that can be cut along the median plane X-X in order to separate said two basically symmetrical parts.

In this connection, it will be appreciated that the elbow parts—i.e., the backs of the book-like configurations—which connect the base branch 10 (and each intermediate branch 12) to the distal branches 14—are set at a distance from the median plane X-X precisely so as not to be involved in the cutting operation performed in the station 102 of FIGS. 19 and 20.

The arrangement is such that the element 1 may be applied with the aforesaid two basically symmetrical parts or halves applied on facing borders of homologous end parts of two of said sanitary products D adjacent to one another in a strip or chain of formation (in this connection see once again FIGS. 19 and 20).

Cutting in the plane X-X, carried out for example in the unit 102 illustrated in FIGS. 19 and 20, separates the two parts or halves of the element 1, leaving them applied, respectively, on one and on the other of the facing ends of two successive products D in the chain of formation.

The fastening element thus obtained can be made in the form of a prefabricated intermediate product (both as regards the general omega-shaped folding, and as regards the application of the glue 16 and, possibly, of the provisional seal formations 23) prior to its application on the sanitary product.

The fastening element 1 can be made in the form of a strip wound in reels and designed to be unwound towards the region where application on the products D is performed.

The application of the element usually entails the use of two layers of glue of the type commonly adopted in the industry of sanitary products aimed at anchorage of the connection element on the facing borders of the homologous lateral end parts of two sanitary products D with, preferentially, application of a third layer of glue in order to fasten the flaps set on the sides of the diaper.

The types of glue considered may be either identical or different from one another.

For example, the glue may be, in the case of the first two layers, of the hot-melt type and, in the case of the third layer, of the evergreen type.

In this case, the first layer of glue, designated by 18, is a virtually continuous layer, which connects the base branch 10 of the element 1 to one of the front ends (the choice between front and rear is not in itself binding) of the product D.

The second layer of glue, designated by 20, is usually divided into two regions or areas, each of which connects one of the distal branches 14 of the fastening element 1 to the opposite side end of the product D.

The third layer of glue, designated by 25, is made (usually with evergreen glue: i.e., a glue which preserves its qualities over time, even following upon repeated detachment-reattachment of the connected parts) in the region or area delimited by the projection of the edges of the elbows that connect the intermediate stretches 12 to the distal stretches 14 on the side end of the product D opposite to the base branch 10.

Upon cutting of the chain of products D along the line X-X, the layer of glue 25 is able to favor adhesion (releasable and refastenable adhesion, if the glue is of an evergreen type)

between the topsheet/backsheet of one of the lateral end parts of the product D and the central portion of the base branch 10 of the connection element.

As will appear more clearly from FIG. 3, after cutting and splaying-out of the product D, the line of connection with evergreen glue 25 extends to closing of the outer stretch of connection between the two lateral end parts of the product D, so preventing discontinuity of any sort and hence achieving (releasable and refastenable) fastening of the flaps set on the sides of the diaper.

In an alternative embodiment, at least one of the layers of glue 18 or 20 may consist of a glue with a degree of adhesion that is sufficiently high as to ensure firm and secure fastening of the product along the waist line in the conditions of normal use, but at the same time such as to enable removal of the product (for instance, once that it has been soiled) by opening it precisely in a position corresponding to the fastening element, which in this case functions, so to speak, as preferential tearing region.

Also in this case, the layer of glue 25 preserves the function described previously.

It will again be appreciated that, in all of the configurations described, the layer 25, if it is made using evergreen glue, can be exploited for keeping the product that has been definitively removed and is to be thrown away packed tightly closed, this being substantially similar to the procedure normally adopted in the case of adhesive stickers for disposable diapers of a traditional type.

The aforesaid configurations of connection can be obtained according to the criteria that will be described more clearly in what follows with reference to FIGS. 19 and 20. It may be preferable to operate by causing the element 1 to be applied on the product D by first making the connection of the distal branches 14 to the corresponding end portion of the product D with the application of the layers of glue 20.

This latter solution presents the advantage that the element 1 thus applied on the strip or web of products D will in any case be closed, in the sense that the two end or distal branches 14 of the omega shape are both firmly connected to the web of products D, without leaving projecting parts that may flap in an uncontrolled way even though the chain or web moves at a rather high speed.

In each case, thanks to the provisional-seal formations 23, whichever the lateral-end part of the product D on which the element 1 is initially applied, since the element itself may be likened to a closed element, it is not in any case exposed to negative phenomena of flapping.

The element 1 can then be set exactly in place, without undergoing deformation or creasing, in the subsequent application station, in which the bottom branch 10 is applied against the corresponding end part of the product D with the application of the layer of glue 18, after prior folding in the form of a U of the products D.

FIG. 3 shows the end result of the operation of separation of the various products D, i.e., when the chain of products D (closed to form a V in the station designated by 100 in FIGS. 19 and 20, so that each assumes the desired configuration of a pair of pants with the waist line closed by means of the fastening elements 1) undergoes cutting along the line X-X in the cutting station 102.

In practice, on each of the sides of the product D (just one of these sides may be seen in the figure in question and in the other homologous figures of the annexed drawings), the two opposite end parts of the product, corresponding to the flaps thereof, are connected together according to a general hinge-like configuration by one of the distal branches 14 (connected to the respective end part of the product D by the layer of glue 20) and by the homologous intermediate branch 12. The latter is connected to the respective end part of the product D thanks to the presence of the layer of glue 16. This layer of glue ensures anchorage of the intermediate branch 12 to a corresponding half of the base branch 10, which is, in turn, connected by a respective portion of the layer of glue 18 to the corresponding end part of the sanitary product.

The intermediate branch 12 extends with continuity of connection to the respective half of the base branch 10. This gives rise to a particularly firm connection, and hence one that is able to withstand any tensile stress to which the fastening element 1 may be subjected during use of the product. It is here evident how the layer of glue 25 ensures releasable and refastenable fastening of the flaps located on the sides and how the distal branch 14 and the intermediate branch 12 provide for shielding of the flap, ensuring a continuous and delicate contact (soft touch) on the hips of the user.

Figure 4:
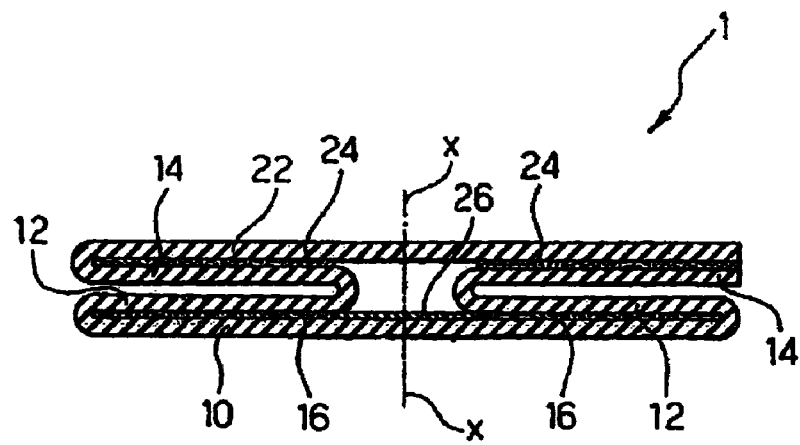
FIGS. 4 to 6 illustrate, according to modalities respectively corresponding to the criteria of representation adopted in FIGS. 1 to 3, another embodiment of a fastening element according to the invention.
Figure 5:
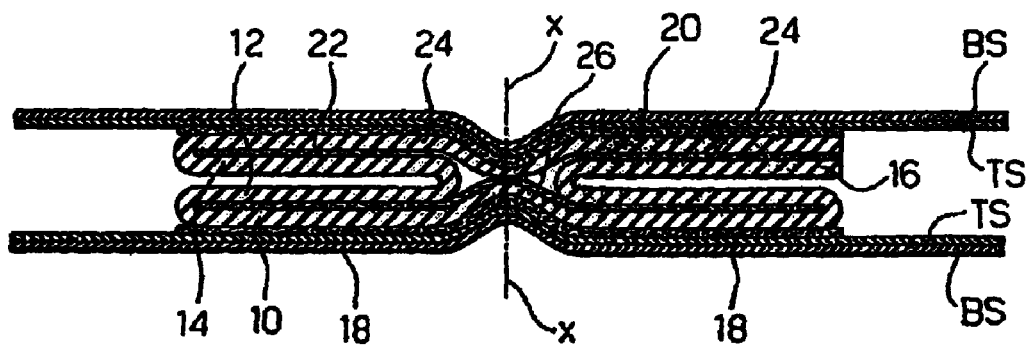
Figure 6:
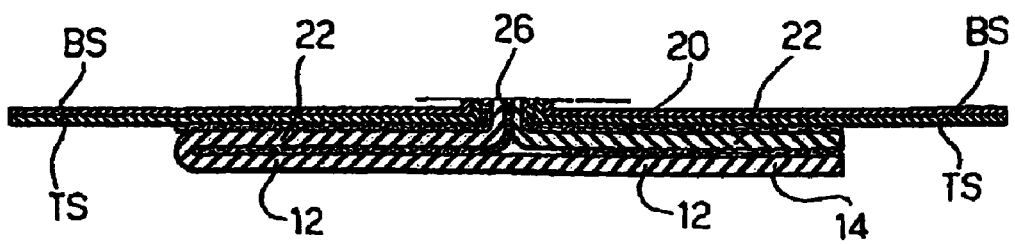

The alternative embodiment illustrated in FIGS. 4 to 6 is, as a whole, similar to the embodiment represented in FIGS. 1 to 3 so that there apply thereto basically all the considerations made previously as regards the embodiment represented in FIGS. 1 to 3. The main difference is represented by the fact that the strip of material (once again this may be, for example, non-woven fabric of the SMS type) extends beyond the base omega-shaped configuration represented in FIGS. 1 to 3 so as to present, as ideal extension of one of the distal branches 14, a further branch 22, which extends in the form of a bridge connecting the two distal branches 14, it being connected thereto by layers of glue 24.

In this case, the modes of application on the product D (exemplified in FIG. 5) envisage application of a layer of glue 20—which this time extends with continuity so as to give rise to the final configuration of connection represented in FIG. 6. This configuration proves particularly firm in so far as the connection between the two end parts of the sanitary product is ensured by two parallel flexible elements defined by corresponding branches of the original omega-shaped element.

In this case, the fastening of the flap located on the sides of the finished product is obtained by applying a layer of glue (for instance, of an evergreen type), designated by 26, which is deposited in the region or area of the base branch 10 delimited by the projection thereon of the edges of the elbows that connect the intermediate stretches 12 with the distal stretches 14 so as to render fastening of the flaps set on the sides of the diaper releasable and refastenable.

The element illustrated in FIGS. 4 to 6 presents the further advantage represented by the fact that it appears right from the start as a closed element with a tubular structure. This means that it is possible, in this case, to prevent application of provisional seal formations for the conservation of the closed-packet structure during processing.

The additional branch 22 (which, like the base branch 10, is to be cut out in the median plane X-X) may in itself also consist of a material different from the material constituting the remaining parts of the element 1.

Figure 10:
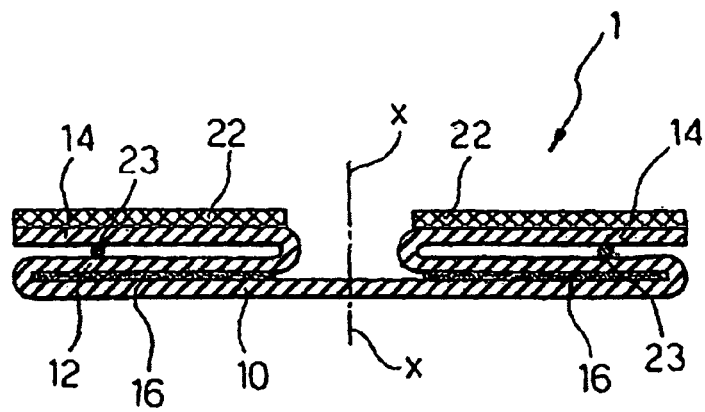
FIGS. 10 to 12 illustrate a possible variant mode of fabrication of the embodiment represented in FIGS. 7 to 9.
Figure 11:
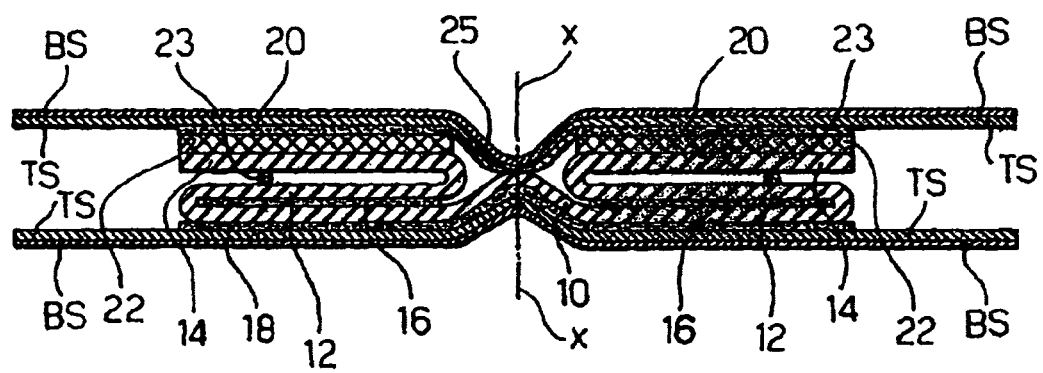
Figure 12:
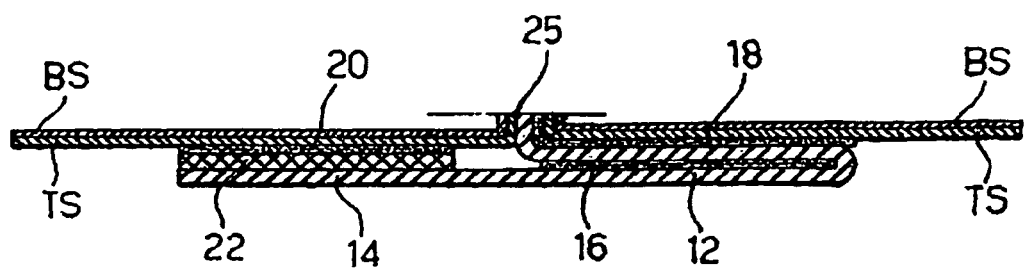

This possibility of differentiation is further shown in the variant of FIGS. 7 to 9 (and also in the solution, which is, as a whole, similar, represented in FIGS. 10 to 12).

The embodiments referred to in FIGS. 7 to 12 are the currently preferred embodiments of the invention. These are aimed at bestowing on the element 1 characteristics of releasability and refastenability.

In this case, in fact, the material constituting the branch 22 (which is here to form an element in itself associated to an omega-shaped structure of the type represented in FIGS. 4 to 6) and the characteristics of the material constituting the remaining part of the element 1 (namely, the distal stretches 14 thereof) are differentiated in such a way that the said two elements present characteristics of disengageable and re-engageable connectability. These are characteristics that can be obtained by bestowing on these complementary elements the characteristics of the parts of a fastening of a microhook (hook-and-loop) mechanical type, or of a fastener of the type commonly referred to as Velcro fastener.

For instance, the branch 22 can be configured in such a way as to carry hook-like parts, which are designed to engage corresponding loop-like parts provided in the distal branches 14.

The said loop-like parts may either be present on the distal branches 14 or form part of the distal branches 14 themselves: for instance, the said distal branches 14 may be made—in a way in itself known—in the form of a non-woven fabric comprising fibers which are sufficiently loose and disconnected from one another as to form loops which can be engaged by the hooks carried by the branch 22.

As may be seen in FIG. 9, the connection structure that may be obtained is substantially similar to the one already illustrated in FIG. 6 (it will be noted simply that FIGS. 6 and 9 are specular with respect to one another), with the important difference represented by the fact that the configuration of connection represented in FIG. 9 is uncoupleable. The branch portion 22 connected to one of the end parts of the sanitary product is in fact selectively disengageable from the distal branch 14 to which it normally adheres, at the same time with the possibility of re-engagement according to the modalities already defined as "releasable and refastenable".

In this case, fastening of the flaps located on the sides of the finished product is obtained thanks to the releasable and refastenable connection of the branch portion 22 and the base-branch portion 10, which are comprised in the flaps.

FIGS. 10 to 12 refer to a solution that is, as a whole, identical to the one represented in FIGS. 7 to 9, with the difference represented by the fact that, instead of being made of a single piece, the branch 22 illustrated in FIGS. 10 to 12 is made up of two separate portions, each of which is to be selectively connected to a respective distal branch 14.

As envisaged in the case of the embodiment illustrated in FIGS. 1 to 3, also for this embodiment it is possible to resort to provisional-seal formations 23 for fixing the intermediate stretches 12 to the corresponding distal stretches 14, thus rendering the element similar to a closed element, and hence, not exposed to any adverse phenomena of flapping. As in the case described previously, the said provisional-seal formation can be made with the application of a spot of evergreen glue or pressure-sensitive glue or by means of a thermo-mechanical-welding spot (heat sealing).

The embodiment illustrated in FIGS. 10 and 12 affords the advantage represented by the fact that, since the branch 22 has a discontinuity in the central portion of the element 1 (hence along the cutting line X-X), it enables a saving in costs to be achieved as compared to the embodiment illustrated in FIGS. 10 to 12 (Velcro-type material is somewhat costly).

As in the embodiment illustrated in FIGS. 1 to 3, a third layer of glue of the evergreen type, designated by 25, is deposited on the side end of the product D opposite to the base branch 10, in the region or area delimited by the projection of the edges of the elbows that connect the intermediate stretches 12 with the distal stretches 14 on said side end, to obtain the releasable and refastenable fastening structure of the flaps located on the sides of the diaper.

Furthermore, in the embodiment illustrated in FIGS. 10 to 12 and in the conditions represented in FIG. 12, the branch 22 (which may consist of quite a rigid element, above all if it is made up of the part provided with microhooks of a structure of the homologous type) is altogether hidden with respect to the outside, a result that is not obtained in the case of the solution referred to in FIG. 9.

Also in the embodiments of FIGS. 7 to 12, the distal branch 14 and the intermediate branch 12 provide for shielding of the flap, ensuring a continuous and delicate contact (soft touch) on the hips of the user.

Figure 13:
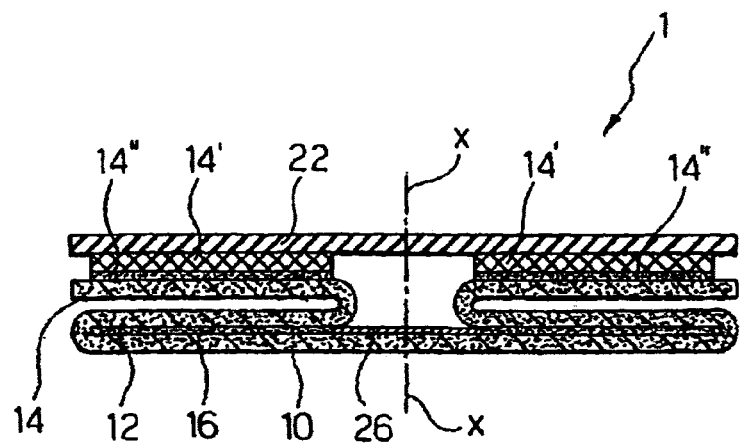
FIGS. 13 to 15 illustrate, according to criteria basically similar to the criteria of representation adopted in FIGS. 1 to 3, yet another embodiment of a fastening element according to the invention.
Figure 14:
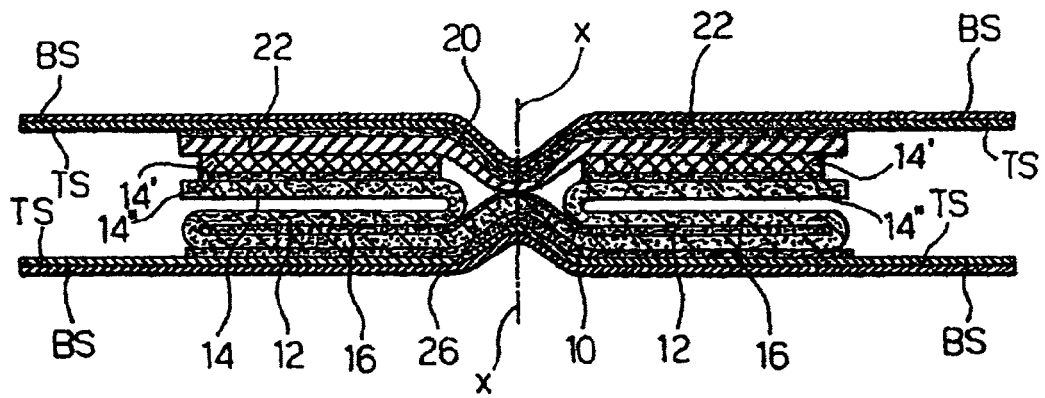
Figure 15:
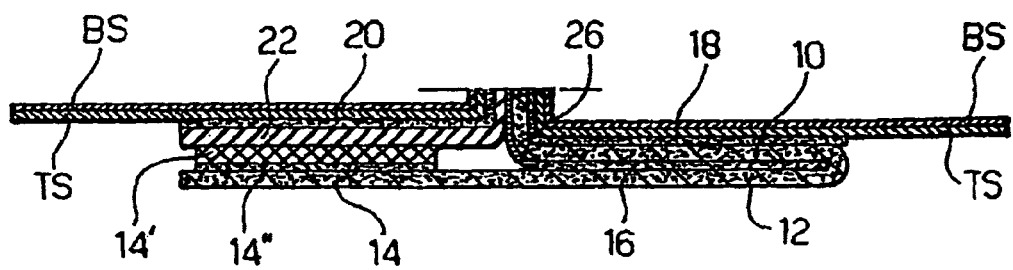

FIGS. 13 to 15 illustrate a further development of the fastening element 1 of a disengageable and re-engageable type, already illustrated with reference to FIGS. 7 to 12.

In the embodiment illustrated in FIGS. 13 to 15, the configuration of connection of the distal branches 14 and of the branch 22 is reversed with respect to the previous cases. In this case, instead of carrying the hook formations of the microhook fastening structure, the branch 22 carries (i.e., incorporates) the parts with loops, whilst the hooks are carried by elements 14' applied by means of respective layers of glue 14" on the distal branches 14 of the omega-shaped base structure.

In this case, considering the configuration after cutting and splaying-out of the product D along the waist line, an element of the microhook fastening system is effectively exposed along the flaps located on the sides: this is, however, the part 22 that carries the loops, whilst the part that carries the microhooks is altogether hidden within the fastening element 1.

As in the embodiment illustrated in FIGS. 4 to 6, fastening of the flaps located on the sides of the finished product is obtained by application of a layer of evergreen glue, designated by 26, deposited in the region or area of the base branch 10 delimited by the projection thereon of the edges of the elbows that connect the intermediate stretches 12 to the distal stretches 14 so as to obtain the releasable and refastenable fastening of the flaps located on the sides of the diaper.

Figure 16:
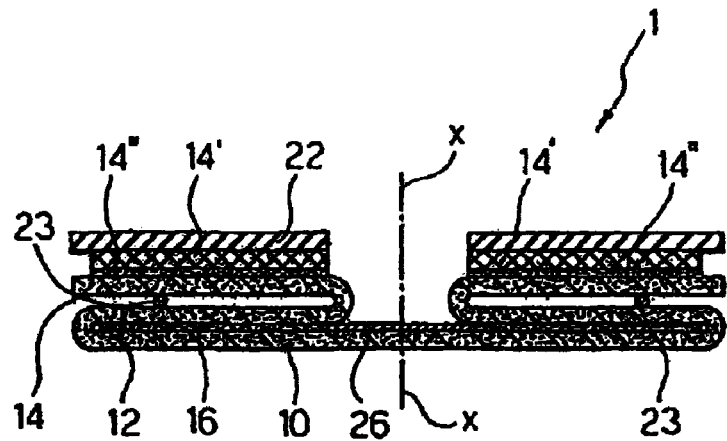
FIGS. 16 to 18 illustrate a possible variant mode of fabrication of the embodiment represented in FIGS. 13 to 15.
Figure 17:
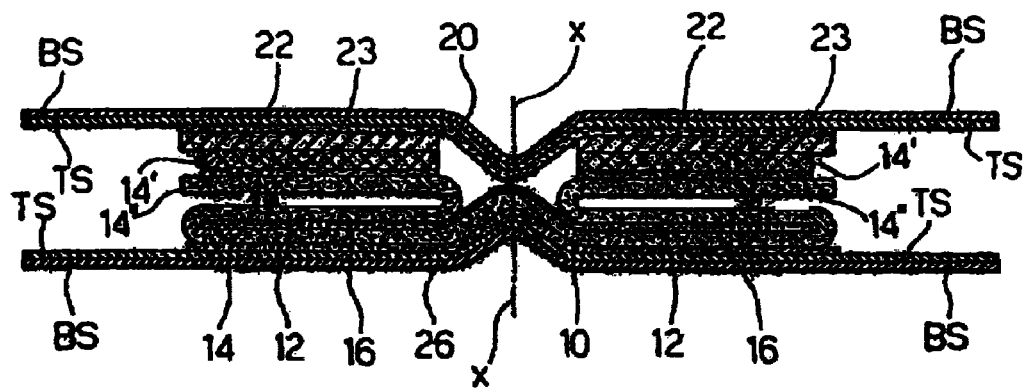
Figure 18:
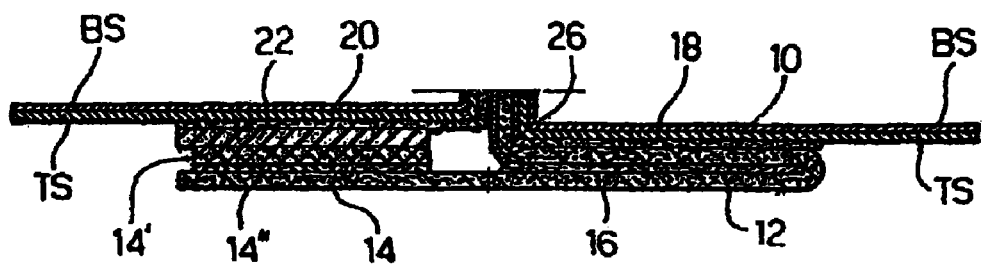

FIGS. 16 to 18 refer to a solution that is, as a whole, identical to the one represented in FIGS. 13 to 15, with the difference represented by the fact that, instead of being made of a single piece, the branch 22 illustrated in FIGS. 16 to 18 is made up of two separate portions, each of which is designed to be selectively connected to a respective distal branch 14'.

As envisaged for the embodiment illustrated in FIGS. 1 to 3 and 10 to 12, also in the case of this embodiment a provisional-seal formation 23 fixes the intermediate stretches 12 to the corresponding distal stretches 14, so that the element may be likened to a closed element, and hence one not exposed to the negative phenomena of flapping. As in the cases previously described, said provisional-seal formation can be obtained with the application of a spot of evergreen glue or pressure-sensitive glue or by means of a thermo-mechanical-welding spot (heat sealing).

The embodiment illustrated in FIGS. 16 and 18 affords the advantage represented by the fact that, since the branch 22 has a discontinuity at the central portion of the element 1 (hence along the cutting line X-X), it enables a saving in costs to be achieved with respect to the embodiment illustrated in FIGS. 13 to 15.

As in the embodiments illustrated in FIGS. 1 to 3 and 10 to 12, a third layer of glue of the evergreen type, designated by 25, is deposited on the side end of the product D opposite to the base branch 10, in the region or area delimited by the projection of the edges of the elbows that connect the intermediate stretches 12 to the distal stretches 14 on said side end, in order to obtain releasable and refastenable fastening of the flaps set on the sides of the diaper.

Also in the embodiments illustrated in FIGS. 13 to 18, the distal branch 14 and the intermediate branch 12 provide for shielding of the flaps, ensuring a continuous and delicate contact (soft touch) on the hips of the user.

There now follows a more detailed description of FIGS. 19 and 20. As has already been said, the figures in question refer to a particularly preferred applicational solution, in which the process of fabrication of the strip-like material designed for being segmented to obtain the fastening elements 1 is integrated (basically as a set of preliminary operations) in the process of application of the elements 1 themselves on the semi-finished pieces D' which are to give rise—via the sequence of operations of folding to form a V (station 100) and of cutting (station 102) already described previously—to the products D.

It will, however, be appreciated that, albeit constituting a currently preferred choice, the fact of integrating the process of fabrication of the elements 1 with the process of application thereof and with the process of fabrication of the products D does not constitute in any way an imperative choice.

The elements 1 are suited for being made in the form of a semi-finished product consisting of a strip-like material that can be cut to length in successive lengths (i.e., segmented) with a view to its application on the products D. The aforesaid semi-finished product constitutes a product in itself, which can be manufactured separately and then be supplied to the subjects that carry out the process of application of the elements themselves in the process of fabrication of the products D.

As will emerge more clearly from what follows, the solutions illustrated in FIGS. 19 and 20 refer principally (but not exclusively) to the fabrication and application of fastening elements 1 corresponding to the embodiments illustrated in FIGS. 7 to 9 and 10 to 12, respectively.

The aforesaid solutions thus present various elements in common. It follows that, in the absence of specific indications aimed at distinguishing one solution from another, what has been said with reference to one solution applies directly also to the other.

Thus, in both of FIGS. 19 and 20, there may be seen the chain of semi-finished pieces D' already described extensively previously, fed in from the left to the right and from the bottom upwards. This chain of semi-finished pieces D' is here assumed to be formed, according to known criteria, by equipment that is likewise known, and hence such as not to require a more extensive description herein.

For reasons of completeness it is recalled that, in the solution illustrated herein by way of example, the semi-finished pieces D' are assumed as already presenting the sandwich structure (topsheet TS and backsheet BS with interposition of an absorbent layer) described previously. Even though this solution is widely preferred, there are certainly not excluded from the scope of the invention solutions in which the aforesaid sandwich structure is obtained in a moment subsequent to or concomitant with the operations described here.

In FIG. 19, the reference 114 designates a station for intermittent application of glue. The station 114 is designed for applying on the chain of semi-finished pieces D'—in exactly determined positions at regular distances apart, corresponding to the positions in which it is desired to arrange the fastening elements 1—areolae of glue which form in practice the layer of glue designated by 18 in FIGS. 7 to 12.

The characteristics of the station 114 and of the glue there applied (for example a glue of the hot-melt type) are to be considered certainly known to the person skilled in the sector of manufacture of absorbent sanitary products.

The station 114 operates in the proximity of the margin of the chain of semi-finished pieces D' designated by F1.

Once again in FIG. 19, the reference 114' designates a further station for the intermittent application of glue. The station 114' is designed for applying on the chain of semi-finished pieces D'—in exactly determined positions at regular distances apart, corresponding to the positions in which it is desired to arrange the fastening elements 1—areas of glue that, in practice, form the layer of glue designated by 25 in FIGS. 1 to 3 and FIGS. 10 to 12.

Also the station 114', like the station 114, operates in the proximity of the margin of the chain of semi-finished pieces D' designated by F1.

In the solution illustrated in FIG. 20, there is envisaged the presence of a station homologous to the station 114, designated by 116, which operates in the proximity of the margin designated by F2. Also the station 116 applies on the chain of semi-finished pieces D'—in exactly determined positions at regular distances apart, corresponding to the positions in which it is desired to arrange the fastening elements 1—areas of glue. In this case, these are areas of glue that form the layer of glue 20.

Once again in FIG. 20, the reference 116' designates a further station for the intermittent application of glue (represented by a dashed line). If present, the station 116' is designed to apply on the chain of semi-finished pieces D'—in exactly determined positions at regular distances apart, corresponding to the positions in which it is desired to arrange the fastening elements 1—areas of glue that, in practice, form the layer of glue designated by 26 in FIGS. 16 to 18.

Also the station 116', like the station 116, operates in the proximity of the margin of the chain of semi-finished pieces D' designated by F2.

In both of FIGS. 19 and 20 the reference 118 indicates a source—this is typically of a reel-type unwinder with the function of fast change of the feeding reel—from which there is wound off a strip 120 of material, such as a non-woven fabric.

The material constituting the strip can present a loop structure that confers thereon the possibility of constituting—without further treatment—the part provided with loops of a hook-and-loop fastening configuration.

In a bending station 122—of a known type—the strip 120 is subjected to an operation of bending to form a C basically corresponding to the formation of the two distal branches 14 (see once again FIGS. 7 and 10) and to the upturning thereof on the parts of the strip 120 designed for subsequently forming the intermediate branches 12 of the element 1.

The reference 124 designates a station used for the embodiment illustrated in FIGS. 1 to 3, 10 to 12 and 16 to 18 for application, on the C-shaped strip formed in the station 122,—in exactly determined positions, at regular distances apart,—the provisional-seal formation 23.

As already described previously, the aforesaid provisional-seal formation 23 entails the establishing of a "technical" connection or tacking (i.e., a non-permanent connection which will be absent in the finished product) between the free ends of the distal branches 14 and the body part of the strip on which said branches are folded back, the purpose being to prevent the aforesaid free ends and/or distal branches 14 as a whole from possibly lifting up, even marginally, from the rest of the strip, and so hindering the subsequent operations of treatment described in what follows.

The aforesaid (preferred, but non-imperative) provisional-seal formation is also obtained according to known criteria, for instance with the application of a so-called technical glue or with a welding spot obtained using systems of thermo-mechanical welding (heat sealing) and, in particular, ultrasonic-sealing systems. By its very nature, the adhesive character of a technical glue is not permanent and ceases to be effective after a certain period of time. Glues of this type are known in the art. For instance, the experiments conducted by the present applicant show that, in the context of the present invention, particularly effective is the use, as technical glue, of the product AL 11 available from, for example, Savaré I. C. S.r.l. of Milan.

The strip, in the position where it is bent to form a C, is sent on to a station for dispensing glue 126, which applies, on the body of the strip, two strips of glue (no longer technical, but permanent, for instance of the hot-melt type) corresponding to the layers designated by 116 in FIGS. 7 to 12.

At this point, the strip advances through a further bending station 126, which (see once again for reasons of clarity FIGS. 7 and 10) performs the upturning of the distal branches 14 and of the intermediate branches 12 on the body (i.e., on the central part of the strip).

In practice, the station 126 performs a further operation of bending in the form of a C with the concavity opposite to that of the operation of bending carried out in the station 122, thus achieving the desired general omega-shaped configuration and bringing about stable connection of the intermediate branches 12 with the central part, i.e., with the omega-shaped base branches 10.

On the structure thus obtained, the element 22 is then applied, which, in the embodiment described herein, carries hook-like parts that can engage in a removable way corresponding loop-like parts present—either intrinsically or in so far as they are applied—on the distal branches 14 of the remaining part of the fastening element.

In the case of the embodiment illustrated in FIGS. 7 to 9, the element 22 is made of a single piece.

The corresponding application equipment, represented in FIG. 19, thus comprises a dispensing reel 128, from which the corresponding strip-like material is wound off towards a roller-type connection station 130. Here the strip carrying the hooks 22 is applied against the distal branches 14, which provide the loops, so achieving a configuration of firm but separable connection. As has been seen, it is this that enables release and refastening of the waistline of the product D along the flaps located on the sides.

In the case of the embodiment illustrated in FIGS. 10 to 12, the element 22 is made up of two pieces, separated by the discontinuity that enables the layer of glue 25 to adhere centrally to the base branch 10 of the fastening element 1. The corresponding application equipment, represented in FIG. 20, thus comprises two dispensing reels 128a and 128b, from which the two portions of strip-like material that are to make up the two branches of the layer 22 are wound off in the direction of the roller-type connection station 130. Here the two portions of strip carrying the hooks 22 are applied against one and the other of the distal branches 14, which provide the loops, also in this case, forming a configuration of firm but separable connection.

In the one case (FIG. 19) and in the other case (FIG. 20), the composite strip thus obtained advances towards an application station 132, in which the strip in question undergoes segmentation so as to form the individual fastening elements 1, which are to be applied by the station 114 on the chain of semi-finished pieces D' in positions corresponding to the adhesive areas.

The application station 132 is usually shaped so as to impart on the lengths that are to form the elements 1a rotation of 90°. This rotation is designed to take into account the fact that the composite strip coming out of the connection station 130 advances lengthwise, i.e., with the ideal plane of cross section, represented in FIGS. 7 and 10, oriented in a direction orthogonal to the direction of advance of the strip, which is collinear with the direction of advance of the chain of semi-finished pieces D'.

At the same time, the elements 1 are applied on the chain of semi-finished pieces D' with the plane X-X of FIGS. 7 and 10 oriented along the homologous line of action of the cutting station 102, i.e., in a direction transverse to the direction of advance of the said chain.

Stations for segmentation and rotation, which have the characteristics described above and which may likewise allow for the considerable difference in speed of advance between the strip coming out of the roller-type connection station 130 and the chain of semi-finished pieces D', are well known in the art, as is witnessed, for example, by the documents EP-A-0 943 305 or EP-A-0 997 123. The said documents, to which reference may be made for a more detailed description of the station 132, are both filed in the name of the holder of the present patent application.

At this point, the chain of semi-finished pieces D', which carry the elements 1 applied at the margin F1, is made to advance towards the station 100, which performs the action of closing to form a V, as already described.

In particular, the representation of FIG. 19 refers specifically to an embodiment in which the sides or faces of the elements 1 which are to be applied against the margin F2 of the chain of semi-finished pieces D' have been previously adhesive-coated, thus rendering them of the self-adhesive type. In this way, there is avoided the need to deposit corresponding areas of glue along the margin F2 of the chain of semi-finished pieces D'.

This result (pre-adhesive-coating) can be obtained—according to known criteria—at the level of the application station 132, for instance by envisaging the presence of an applicator assembly (not illustrated in the drawings), which applies—before or after segmentation of the strip from which the elements 1 are formed—a film of glue on the side or face of the element that is to undergo pre-adhesive-coating, and by configuring the gripping elements of the application station 132 so that they may perform on the elements 1 the necessary function of picking-up and transfer, so preventing any undesirable adhesive connection with the elements 1 themselves. This result can be obtained, for example, by providing the application station 132 with ice-film gripping elements.

It goes without saying that the pre-adhesive-coating can be provided—also here by resorting to measures in themselves known—on both of the faces or sides of the elements 1, thus rendering superfluous the application of areas of glue along both of the margins F1 and F2 of the chain of semi-finished pieces D'.

The choice of one particular solution rather than another is evidently dictated by the specific applicational requirements. Recourse to the pre-adhesive-coating (on one or both of the sides) has the undoubted advantage of rendering less critical the synchronization between the application station 132 and the movement of advance of the chain of semi-finished pieces D'. It is evident that, in the case of the pre-adhesive-coating, a synchronization such as to prevent an excessively rough positioning of the elements 1 is sufficient, in view of the fact that it is no longer necessary to ensure the level of precision such as to cause each element 1 to be positioned exactly, in a centered way, on a corresponding areola of glue.

Once again with reference to FIG. 19, the strip 22 is anchored on the homologous borders (still connected together—in so far as they are designed to be separated only subsequently by the action of the cutting unit 102) of the side ends facing two semi-finished pieces D' that are adjacent in the chain, by means of an adhesive layer present on the back of said strip 22, i.e., appropriately applied thereon by the station for intermittent application of glue 131, which is of the same type as the station 114.

With reference to FIG. 20, the strip 22 is anchored on said homologous borders of the side ends facing two semi-finished pieces D' adjacent in the chain, by means of the application on the topsheet TS to which the layer 22 is to be connected (see in this regard FIGS. 8 and 11) of areas of glue corresponding to the layers designated by 20 in FIGS. 8 and 11. Given the firm and precise anchorage of the element 1 on the chain of semi-finished pieces D' obtained by means of the station 132, the glue of the layer 20 can be applied either on the back of the layer 22 by the station 131 (see in this regard FIG. 19) or on the topsheet TS to which the layer 22 is to be connected (see in this regard FIG. 20). Furthermore, precisely on account of its "closed" configuration, the element 1 proves stable in shape and free from any phenomena of flapping, so that, even when the station 100 is made to function at a high speed, it is possible to rely on the fact that the areas of glue 20—whether applied on the topsheet of the semi-finished pieces, or applied on the back of the strip 22—will always end up being positioned exactly between these two elements, so as to be able to perform its function correctly.

The semi-finished pieces D', which are at this point closed so as to form a V shape, advance towards the cutting station 102, where, according to the operating procedure described previously, the individual products D are formed.

Preferentially, between the closing station 100 and the cutting station 102 there is present a station 134 designed for clinching and consolidating, with an action of compression, the connection between the fastening elements 1 and the portions of topsheet TS, between which each element 1 is comprised in the finished product D (here again see, for example, FIGS. 8 and 11).

It will be appreciated that this consolidating action is performed also in regard to the microhook connection established between the layer 22 and the distal branches 14, as well as in the case of the embodiment illustrated in FIGS. 10 to 12, in regard to the connection between the adhesive layer 25 and the central part of the base branch 10.

In a currently preferred embodiment, the station 134 has a general configuration that may be likened to that of a belt press with a motor-powered closed-loop mobile pressing formation, which may basically be likened to a track that presses the products D with its active branch, located in the bottom position and mobile in a way concordant and synchronized with the chain of products D.

The action of pressure may be applied either against a plane of sliding, on which the products D slide, or, in a preferred way, against an underlying belt conveyor (not visible in the drawings), which ensures conveying of the products D, i.e., against a track formation that is altogether identical to what may be seen in the drawings, but located under the plane of advance of the products D.

In a preferred way, the track formation or formations in question have teeth 134a in positions corresponding to those occupied by the microhook connection between the layer 22 and the distal branches 14, i.e., in the case of the embodiment illustrated in FIGS. 10 to 12, of the connection between the adhesive layer 25 and the central part of the base branch 10.

The track formations in question operate so as to apply the same vertical compressive pressures adequate for ensuring fastening of the flaps set on the sides, so preventing application on the remaining parts of the fastening element 1 of excessively strong vertical compressive pressures such as might squeeze them excessively. It will be appreciated that, by selectively adjusting the intensity of the action of compression exerted on the products D by the formation 134, it is possible to regulate precisely (in the case of embodiments of the type illustrated in FIGS. 9 to 12) the intensity of the connection between the layers 22 and the distal branches 14. It is thus possible to adjust the intensity of the reaction opposed by the elements 1 to any attempt to open the waistline of the products D that is precisely aimed at separating the layers 22 and the distal branches 14 from one another.

The teeth 134a make it possible to bestow on the element 1 (even before it arrives at the cutting station 102) the general hourglass configuration that may clearly be seen in FIGS. 2, 5, 8, 11, 14 and 17, which, after cutting of the element along the line X-X, lies at the basis of the fastening (which may be releasable and refastenable, according to the criteria repeatedly referred to previously) of the flaps located on the sides of the product.

In other words, the teeth 134a enable the appropriate connection formation provided in the median plane X-X (layers of glue 25 or 26, central stretch of the microhook formations which operate in a position homologous to these layers of glue) to act between the borders B1, B2 that are set facing one another.

Figure 21:
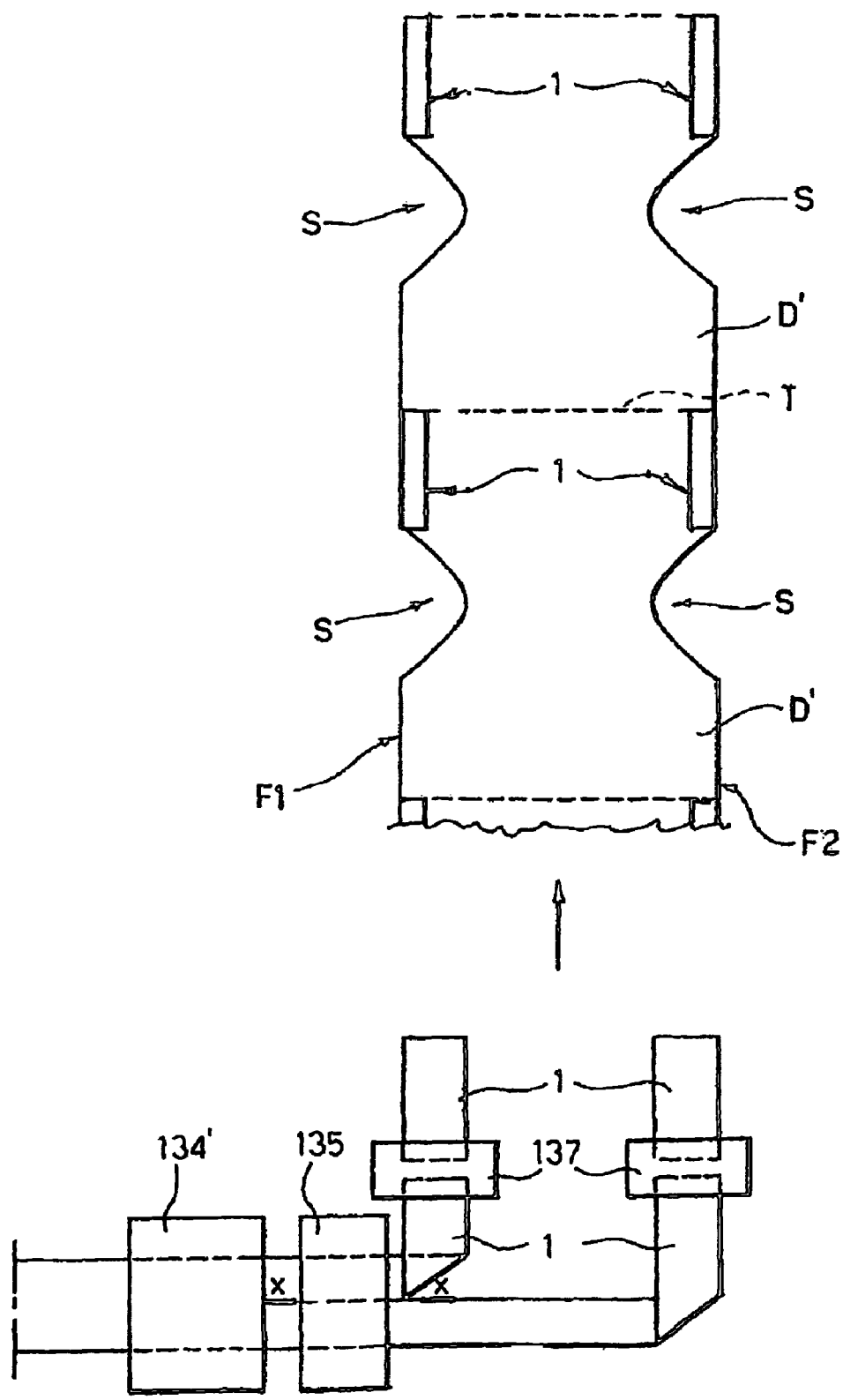
FIGS. 21 and 22 are schematic illustrations of possible alternative embodiments of the solutions illustrated in FIGS. 19 and 20.
Figure 22:
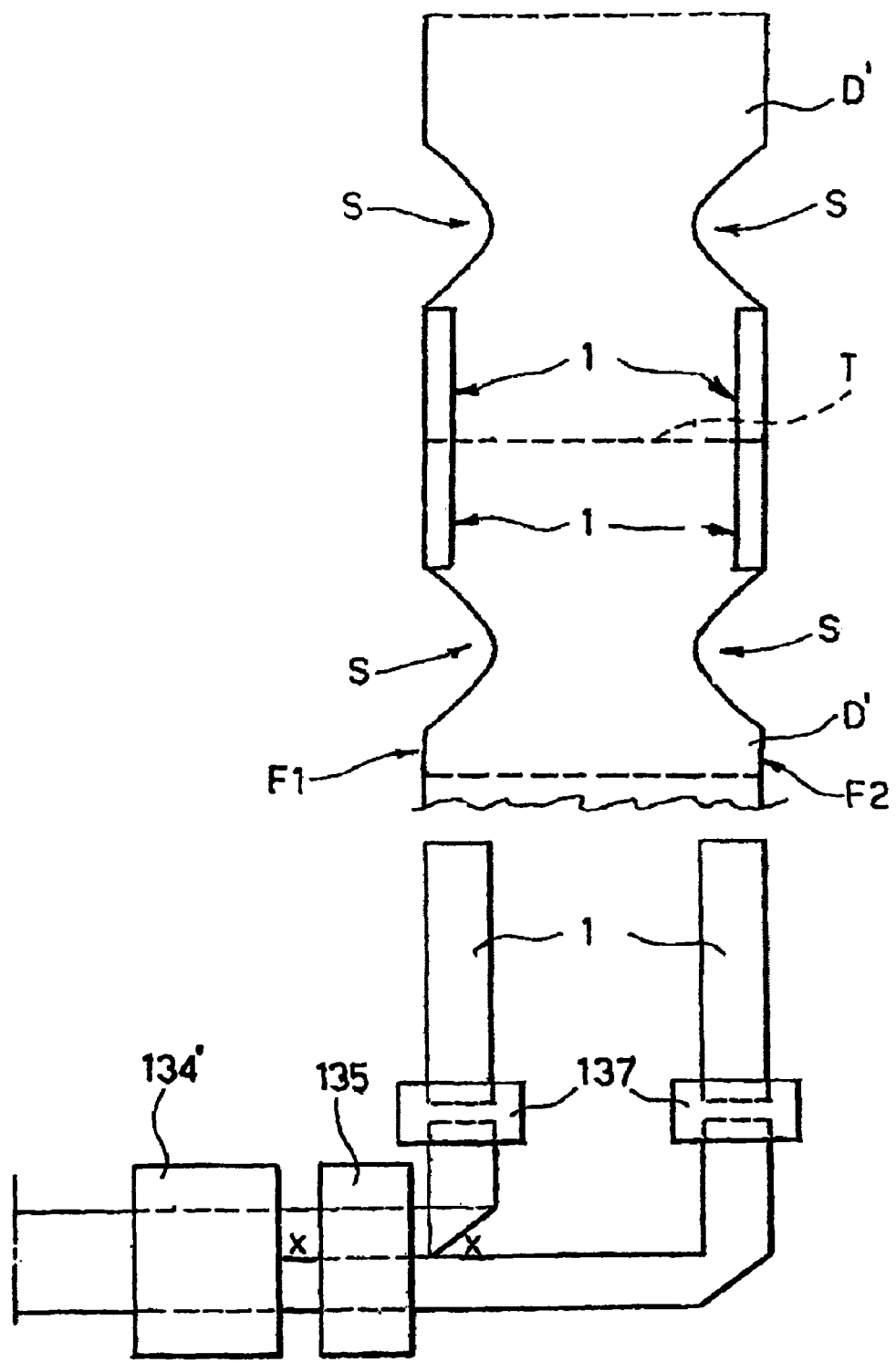

FIGS. 21 and 22 are schematic illustrations of the possibility of using the fastening element 1 described previously (in any of the embodiments considered) in the context of a process of fabrication of sanitary products D in which the strip, web or chain of semi-finished pieces D' is constituted by semi-finished pieces connected together not crosswise—as in the case of the solutions illustrated in FIGS. 19 and 20—but lengthwise.

In a process of this type (which is at times referred to as machine-direction process, i.e., one carried out in the direction of the machine), the various semi-finished pieces D' advance lengthwise, i.e., with their end parts aligned in the direction of advance, with the rear end of one semi-finished piece connected to the front end of the semi-finished piece following it in the chain (see the top part of FIGS. 21 and 22). Of course, "front" and "rear" here refer to the direction of advance of the chain (from the bottom upwards in FIGS. 21 and 22), and not to the way in which the product D will be worn.

The various semi-finished pieces D' of the chain are then separated along lines of cutting T using equipment basically similar to the cutting station 102 that may be seen in FIGS. 19 and 20 so as to give rise to the individual products D.

Also in this case, it must be assumed that the process of fabrication referred to herein is in itself known in its essential terms. This applies also to the final processing step (not explicitly illustrated in FIGS. 21 and 22), in which the individual products D obtained as shown in the top part of the aforesaid FIGS. 21 and 22 are closed to form a U or a V in order to bestow thereon the desired pant-like configuration.

As regards the fabrication of the strip-like element from which the individual fastening elements are obtained, it may be assumed that the alternative solutions represented in FIGS. 21 and 22 basically reproduce the solutions illustrated in FIGS. 19 and 20 up to the roller-type connection station 130.

From here, in the solutions illustrated in FIGS. 21 and 22, the aforesaid strip-like element passes into a station 134', which has a function basically similar to that of the station 134 of FIGS. 19 and 20, i.e., that of pressing the strip-like element centrally in the plane X-X so as to bestow thereon the general hourglass pattern that may be seen in FIGS. 2, 5, 8, 11, 14 and 17. Of course, whilst the station 134 of FIGS. 19 and 20 finds itself operating in a crosswise direction with respect to the direction of advance of the chain of semi-finished pieces D' (on which the elements 1 have been applied after being rotated by 90° in the station 132), the station 134' of FIGS. 20 and 21 operates lengthwise, and can be usefully made up of two ribbed counter-rotating wheels or rollers, which impress the hourglass-shaped pattern on the strip-like element that advances in the space or gap defined between said wheels or rollers.

Set cascaded to the station 134' is a cutting station 135, which—again operating lengthwise—brings about the division of the strip-like element (which, in effect, can now be equated with the element 1) in the plane X-X, i.e., dividing the strip-like element 1 into two basically symmetrical parts.

The structure of the station 135 may basically be identical to that of the station 134' just described. Indeed, the two stations 134' and 135 can be fused into a single station that performs both shaping to form the hourglass configuration and cutting of the element 1 in the plane X-X.

From here, the two parts of the element 1 are sent on to the chain of moving semi-finished pieces D' to be applied on the semi-finished pieces themselves, one on the left-hand side F1 and one on the right-hand side F2 of the chain in question. Of course, also in this case, the terms "right-hand" and "left-hand" are used in reference to the graphic representation of FIGS. 21 and 22 and do not bear any direct relation to the way in which the product D is worn.

Prior to being applied on the semi-finished pieces D' (an operation that is carried out via a machine which is basically similar to the station 132 illustrated in FIGS. 19 and 20), the two branches or parts of the strip-like element are segmented into lengths in a transverse cutting station, designated by 137.

FIGS. 21 and 22 show a solution in which, in the stretch between the longitudinal cutting station 135 (i.e., for cutting along the plane X-X) and the cutting station 137 (usually one for each side of the chain of semi-finished pieces D'—even though it is possible to use a single station operating on both sides), the parts of the element 1 are subjected to a rotation of 90°.

This rotation may be imparted on the elements elsewhere (for instance, in the station 132), but may not even be required at all if the element 1 is already formed lengthwise, i.e., in the direction of advance of the chain of the semi-finished pieces D', as illustrated (albeit in a different context) in FIGS. 19 and 20.

For the application of the individual elements 1 on the semi-finished pieces D' it is possible to adopt different solutions.

For example, FIG. 21 shows a solution in which there exit from the cutting stations 137 lengths which are as long as the individual element 1 (or, rather, as long as the individual part of element 1) that is to be applied on the lateral facing borders of the end parts of the individual product D so as to close the individual product at both of its side flaps.

In this case, on each side of the chain (F1 or F2), there is applied an individual part of element 1 in a position which, after cutting has been performed along the line T, will correspond to the front end or rear end of the individual product D. In this case, the mode of application of the elements 1 is identical for each product D.

FIG. 22 illustrates, instead, a solution in which there exit from the cutting stations 137 lengths that are twice as long as the individual element 1 (or, rather, twice as long as the individual part of element 1) that is to be applied on the lateral facing borders of the end parts of the individual product D so as to close the individual product at both of its side flaps.

In this case, on each side of the chain (F1 or F2), there is alternately applied an ensemble made up of two parts cascaded with respect to one another, each of which will constitute a fastening element applied on the front end or rear end of the individual product D—only after cutting has been performed along the line T. In this case, the procedure for application of the elements 1 is different and alternated for the products D; namely, one product D will come out with the fastening elements 1 applied on the front end, whereas the next one will have the fastening elements 1 applied on the rear end.

Of course, it is also possible to modify the criterion represented in FIG. 22 by applying the piece of double length coming out of the stations 137, once on the side F1 and once on the side F2, with an alternating pitch equal to the length of the individual product D.

Basically, the solutions illustrated in FIGS. 21 and 22 have in common with the solutions illustrated in FIGS. 19 and 20 the idea of making the fastening elements 1 starting from a strip-like element.

In the solutions illustrated in FIGS. 21 and 22 there is envisaged the operation of cutting (in the station 135) the aforesaid strip-like element in the intermediate plane X-X so as to separate the two parts of the fastening element 1 prior to its application on the corresponding sanitary product D. The aforesaid parts of fastening element 1 are then applied to each of the two opposite longitudinal sides F1, F2 of the chain of semi-finished pieces.

In the solution illustrated in FIG. 21, this is done by applying the aforesaid parts of fastening element 1 in the form of segments, each of which is associated to one end of a respective semi-finished piece D' comprised in said chain.

In the solution illustrated in FIG. 22, this is obtained, instead, by applying the aforesaid parts of fastening element 1 in the form of segments (of double length), each of which is associated to the end of two semi-finished pieces D' of the chain. The subsequent segmentation of the chain along the lines indicated by T, leads to the separation of the semi-finished pieces D' connected to one another at said end parts, with the formation of individual products D. The operation of segmentation likewise divides the aforesaid double segments into two portions, each of which is associated to one end of a respective product D.

As has already been said, the final processing step, in which the individual products D obtained as represented in the top part of the aforesaid FIGS. 21 and 22 are closed to form a U or a V in order to bestow thereon the desired pant-like configuration, is not explicitly illustrated in FIGS. 21 and 22. The same applies as regards the application of the area of glue or the formation of the welding areas that secure the fastening elements 1 on the ends of the semi-finished pieces D'. For this purpose, there are applied, with the necessary modifications made, the same technical solutions already described with reference to FIGS. 19 and 20. This applies also as regards the possible pre-adhesive-coating of the elements 1.

The solutions described previously with reference to FIGS. 19 to 22 thus enable production of an absorbent sanitary product which can be worn like a pair of pants and which comprises two end parts that present, on each side of the product, homologous lateral facing borders, which can be connected together so as to define the waist line and the passage for legs of the product itself. On each side of the product, the aforesaid lateral facing borders are connected together by one of the aforesaid two parts or halves of a fastening element 1 of the type described. Each of the parts or halves in question in turn comprises a base branch 10, connected to one of the aforesaid end parts of the product D, and a distal branch 14, connected to the other of the end parts of the same product D, completing its fastening on the waist. The base branch 10 and the distal branch 14 are connected together according to a general book-like configuration open towards the inside of the sanitary product, so that the tensile stresses exerted along the waist line of the sanitary product are sustained as a result of the connection between the base branch 10 and the distal branch 14.

Figure 23:
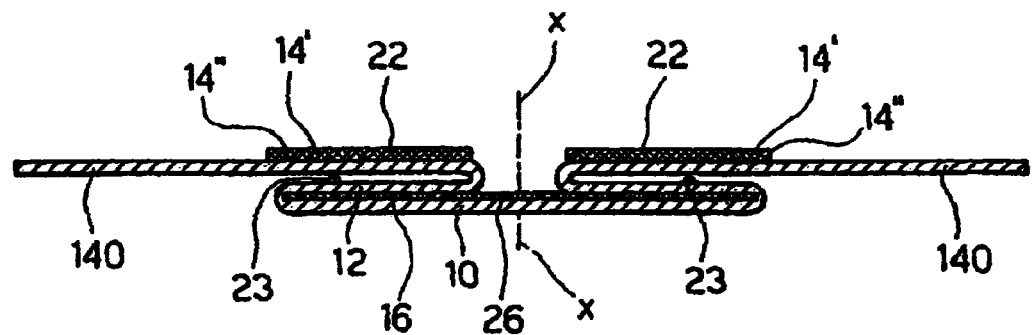
FIGS. 23 to 25 illustrate a still further possible variant mode of fabrication of the embodiment represented in FIGS. 16 to 18.
Figure 24:
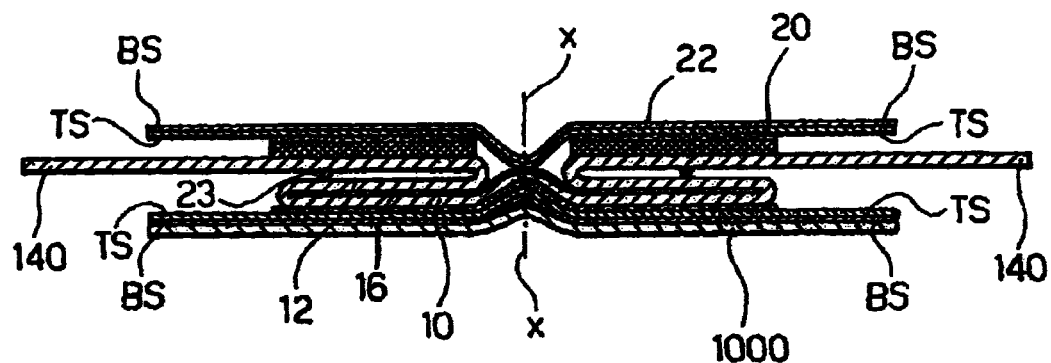
Figure 25:
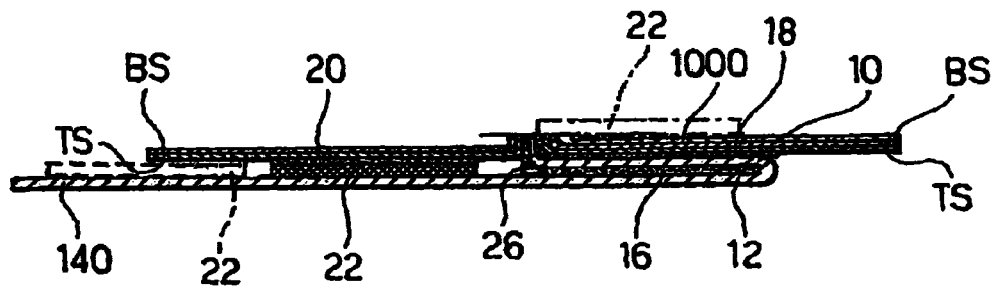

FIGS. 23 to 25 show a still further possible variant mode of fabrication of the fastening element described herein. This variant is intended to take into account the fact that absorbent sanitary products of the "training pant" or "undergarment" type can be used with increased comfort if the possibility exists of inspecting the product while being used (i.e., worn) and/or adapting the "fit" of the product to the wearer by selectively increasing/decreasing the length of the waist line.

Specifically, FIGS. 23 to 25 show how the embodiment shown of FIGS. 16 to 18 can be modified to permit the product to be opened and refastened, while also providing the possibility of varying the length of the waist line of the product.

In the embodiment shown this result is achieved by making it possible to:

selectively vary (as shown by way of example at the lower left-hand side of FIG. 25) the position where the hook element 22 engages the distal branch 14 of the fastening element 1 to which the hook element is associated, and/or selectively vary (as shown by way of example at the upper right-hand side of FIG. 25) the position where the hook element 22 in question engages the opposed outer surface of the facing side edge (or flap) of the product.

To achieve the former result, the distal branch 14 to which the hook element 22 is currently associated is extended as indicated at 140, so that each distal branch 14 is in fact longer that the homologous intermediate branch 12: this fact can be promptly appreciated by direct comparison of FIGS. 16 and 17, on the one side, and FIGS. 23 and 24, on the other side.

Stated otherwise, in the embodiment shown the connection structure of the releasable and refastenable type (i.e., the hook element 22) is adapted to be associated to the distal branch 14 at a plurality of different positions, whereby the length of the waist line of said absorbent sanitary product 1 is selectively adjustable. Preferably, this is achieved simply by making the distal branch 14 longer (as shown at 140) than said the connection structure 22 of the releasable and refastenable type.

In that way, the product 1 may be easily opened (thus having i.a. the possibility of inspecting its state of use) by simply pulling the backsheet/topsheet portion carrying the hook element 22 in order to separate the hook element 22 from the underlying distal branch 14 to which the hook element 22 is currently associated.

Once opened, the product may be re-closed (refastened) with the possibility of coupling the hook element 22 to the distal branch 14 at a position as schematically shown in dotted lines in FIG. 25, that is a position different from the position where the hook element 22 was originally coupled to the distal branch 14. In that way the length of the waist line of the product (i.e., the "fit" to the wearer) can be selectively varied.

This typically occurs by arranging the hook element 22 farther away from the intermediate branch 12, which leads to increasing the length of the waist line and giving the product a "looser" fit to the wearer's body.

The latter result referred to in the foregoing may be achieved by means of a further "hook engageable" (i.e., loop) surface as indicated by reference numeral 1000 in FIGS. 24 and 25. Specifically, the further hook engageable surface 1000 is provided in correspondence with the outer side of the backsheet/topsheet pair carrying the base branch 10. The hook engageable surface in question may be provided in the form of a loop insert applied, e.g., by gluing, the outer side of the backsheet/topsheet pair carrying the base branch 10 or by making, at least locally, the backsheet element BS of the backsheet/topsheet pair in question in the form of a loop material adapted for engagement by the hook element 22.

By providing the surface 1000, the product, once opened, may be re-closed (refastened) with the possibility of coupling the hook element 22 to the surface 1000 as schematically shown in chain line in FIG. 25. This is again a position different from the position where the hook element 22 was originally coupled to the distal branch 14, thus once again giving the possibility of selectively varying the length of the waistline of the product.

In this latter case, this occurs by arranging the hook element 22 over the opposed outer surface of the facing side edge (or flap) of the product, which leads to decreasing the length of the waist line and giving the product a "tighter" fit to the wearer's body.

Stated otherwise, according to the latter feature considered, in each said pair of the homologous facing side edges that can be connected together to close the product along the waistline of the wearer:

on one facing edge, the distal branch 14 of the fastening element 1 has associated therewith a microhook fastener 22, and the other facing edge has a surface 1000 adapted to be engaged by the microhook fastener 22 in a releasable and refastenable relationship.

The microhook fastener 22 is thus adapted to be associated to the facing side of a homologous end part at a plurality of different positions to selectively adjust the length of the waist line of said absorbent sanitary product 1.

The other facing edge in question may either carry an element with loops adapted to be engaged by the microhook fastener 22 or be made of a material with loop structure. In this latter case, the loops of the loop structure constitute the loops that can be selectively engaged by the hooks of the microhook fastener 22.

Those of skill in the art will promptly appreciate that while the combination of the features of i) extending the distal branches 14 and ii) providing the surface 1000 represents a preferred embodiment permitting the length of the waist line of the product to be both increased and decreased to a larger extent, the possibility exists of resorting even to just either of those features.

Similarly, those of skill in the art will promptly appreciate that either or both of these features can be applied to embodiments of the arrangement described herein different from that shown in FIGS. 16 to 18.

There has been described herein a fastening element that may be configured as a sort of closed packet, free from any folds or similar configurations that might open out at the moment of cutting, transfer and positioning of the element on the structure of absorbent articles, such as diapers. The element in question preferentially has an omega-shaped base structure, obtained, once again preferentially, with the use of a single material for the principal constituent element.

There is thus obtained a fastening element which, thanks to the structure and to the material used for the main constituent element, makes it possible to obtain a continuous and delicate contact (soft touch) on the hips of the user, so preventing the risk of causing any irritation or cutting of the skin.

Also described herein is the possibility of making an absorbent sanitary product which can be worn like a pair of pants, with the flaps located on the sides closed, but with the possibility of being opened and refastened, in which the user is altogether prevented from forcing, by gripping the free flaps, the connection between the parts of the fastening element (in particular in the versions in which this is provided for being refastenable), so causing the undesirable release of the waist line of the product.

Of course, without prejudice to the principle of the invention, the details of fabrication and the embodiments may vary widely with respect to what is described and illustrated herein, without thereby departing from the scope of the present invention, as defined by the annexed claims.

In particular, it will be appreciated that the details of implementation illustrated herein with reference to each given embodiment, are understood as being freely transferable to one or more of the other embodiments illustrated. Furthermore, it will be appreciated that the solutions of connection described herein with reference to mechanisms of adhesive connection can be replaced by equivalent solutions, which envisage, for instance, the use of mechanisms of connection by means of heat sealing and/or ultrasonic sealing.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A process for making absorbent sanitary products, each sanitary product having opposed end parts which can be selectively connected so as to define a waist line of the sanitary products, the process comprising:
    forming a chain of semi-finished pieces of the sanitary products, in which adjacent semi-finished pieces in the chain are connected to one another at the end parts so as to form at least one connection region between successive pairs of semi-finished pieces in the chain;
    applying a fastening element having a strip-like body in the at least one connection region of each successive pair of semi-finished pieces, the strip-like body of the fastening element having a base branch portion, opposing distal branch portions and intermediate branch portions, the opposing distal branch portions integrally connected to the base branch according to a general book-like configuration via the intermediate branch portions; and
    segmenting the chain of semi-finished pieces of sanitary products and the fastening elements in the connection regions.

2. The process according to claim 1, further comprising:
    providing each of a first side and a second side of one of the opposed end parts of each sanitary product with a surface adapted to be engaged by a respective microhook fastener of the other one of the opposed end parts in a releasable and refastenable relationship to selectively adjust the length of the waist line of the absorbent sanitary product.

3. The process according to claim 2, further comprising:
    applying onto each of the first side and the second side of the one opposed end part an element with loops adapted to be engaged by the respective microhook fastener.

4. The process according to claim 2, further comprising:
    making each of the first side and the second side of the one opposed end part with a material having loops which can be selectively engaged by the respective microhook fastener.

5. The process according to claim 1, further comprising:
    prior to segmenting, folding the semi-finished pieces of the sanitary products according to a general V-shaped configuration, bringing the opposed end parts of each semi-finished piece into a position facing one another with interposition of the fastening elements.

6. The process according to claim 5, further comprising:
    pressing the opposed end parts of the sanitary products together with the fastening elements therebetween.

7. The process according to claim 6 wherein pressing is performed by applying pressure primarily on an area corresponding to a central part of each of the fastening elements to ensure fastening of the opposed end parts are set on the sides of the sanitary product.

8. The process according to claim 5 wherein applying the fastening element includes applying the fastening element on the chain of semi-finished pieces in the proximity of one of a side margin of the chain and connecting the fastening element to an opposite margin of the chain of semi-finished pieces in concomitance with or after the folding.

9. The process according to claim 1 wherein forming the chain of semi-finished pieces of the sanitary products includes forming the chain of semi-finished pieces with the semi-finished pieces adjacent in the chain connected to one another at side edges of the opposed end parts, so that the connection regions have a center line which extends in a transverse direction with respect to a principal direction of extension of the chain of semi-finished pieces of sanitary products;
    wherein applying the fastening elements to the connection regions includes applying the fastening elements to the connection regions with intermediate planes of the fastening elements aligned with the center lines of the connection regions; and
    wherein segmenting the chain of semi-finished pieces of sanitary products includes segmenting the chain of semi-finished pieces at the center lines of the connection regions, causing the cutting of the fastening elements in the intermediate planes.

10. A process for making absorbent sanitary products, each sanitary product having opposed end parts which can be selectively connected so as to define a waist line of the sanitary products, the process comprising:
    forming a chain of semi-finished pieces of the sanitary products with the semi-finished pieces adjacent in the chain connected to one another at the opposed end parts, with the connection of the opposed end parts aligned perpendicularly with respect to a principal direction of extension of the chain of semi-finished pieces;
    cutting a fastening element in an intermediate plane in order to separate the fastening element into two parts, the fastening element having a strip-like body including a base branch portion, opposing distal branch portions and intermediate branch portions, the opposing distal branch portions integrally connected to the base branch according to a general book-like configuration via the intermediate branch portions;

applying the two parts of fastening element at respective opposite longitudinal sides of the chain of semi-finished pieces; and segmenting the chain of semi-finished pieces of sanitary products by separating the semi-finished pieces connected to one another at the opposed end parts.

11. The process according to claim 10, further comprising:

applying the parts of fastening element at the respective opposite longitudinal sides of the chain in the form of segments, each of which is associated to one end of an adjacent semi-finished piece comprised in the chain.

12. The process according to claim 10, further comprising:

wherein applying the two parts of the fastening element includes applying the two parts of the fastening element at the respective opposite longitudinal sides of the chain in the form of segments, each of which is associated to the ends of adjacent semi-finished pieces in the chain; and wherein segmenting the chain of semi-finished pieces of sanitary products includes segmenting the chain of semi-finished pieces by separating the semi-finished pieces connected to one another at the opposed end parts, the segmenting dividing the segments of each of the two parts of the fastening element into two portions, each of which is associated to one end of an adjacent sanitary product.

* * * * *